(12) United States Patent
Raulf et al.

(10) Patent No.: US 7,811,767 B2
(45) Date of Patent: Oct. 12, 2010

(54) METHODS AND COMPOSITIONS FOR ASSESSING ACUTE REJECTION

(75) Inventors: Friedrich Raulf, Freiburg (DE); Pierre Saint-Mezard, St. Louis (FR); Hai Zhang, Binningen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/282,029

(22) PCT Filed: Mar. 13, 2007

(86) PCT No.: PCT/EP2007/002212

§ 371 (c)(1),
(2), (4) Date: Sep. 8, 2008

(87) PCT Pub. No.: WO2007/104537

PCT Pub. Date: Sep. 20, 2007

(65) Prior Publication Data

US 2009/0022730 A1    Jan. 22, 2009

(30) Foreign Application Priority Data

Mar. 15, 2006    (GB)    ................... 0605217.9

(51) Int. Cl.
*C12Q 1/68* (2006.01)
*G01N 33/53* (2006.01)

(52) U.S. Cl. .......................................... 435/6; 435/7.1

(58) Field of Classification Search ....................... None
See application file for complete search history.

(56) References Cited

U.S. PATENT DOCUMENTS 5,962,301 A    10/1999    Horvitz et al. .............. 432/226

FOREIGN PATENT DOCUMENTS

| EP | 1 780 542 | 5/2007 |
|----|-----------|--------|
| WO | 2004/018710 | 3/2004 |
| WO | 2005/054503 | 6/2005 |
| WO | 2005/117943 | 12/2005 |
| WO | 2006/003927 | 1/2006 |
| WO | 2006/125301 | 11/2006 |

OTHER PUBLICATIONS

Inkinen et al., "DNA Microarray-Based Gene Expression Profiles of Cytomegalovirus Infection and Acute Rejection in Liver Transplants", Transplantation Proceedings, vol. 37, No. 2, pp. 1227-1229, (2005).

Flechner S M et al., "Kidney Transplant Rejection and Tissue Injury by Gene Profiling of Biopsies and Peripheral Blood Lymphocytes", American Journal of Transplantation, vol. 4, No. 9, pp. 1475-1489, (2004).

Akalin E et al., "Gene Expression Analysis In Human Renal Allograft Biopsy Samples Using High-Density Oligoarray Technology", Transplantation, vol. 72, No. 5, pp. 948-953, (2001).

Sarwal M et al., "Molecular Heterogeneity in Acute Renal Allograft Rejection Identified by DNA Microarray Profiling", New England Journal of Medicine, vol. 349, No. 2, pp. 125-138, (2003).

*Primary Examiner*—James Martinell
(74) *Attorney, Agent, or Firm*—Leslie Fischer

(57) ABSTRACT

The invention relates to the analysis and identification of genes that are up-regulated simultaneously in transplant rejection. This simultaneous up-regulation of genes provides a molecular signature to accurately detect transplant rejection.

14 Claims, 7 Drawing Sheets

METHODS AND COMPOSITIONS FOR ASSESSING ACUTE REJECTION

BACKGROUND OF THE INVENTION

Despite clinical application of potent immunoregulatory drugs and biologic agents, acute rejection remains a common and serious post-transplantation complication. It is also a risk factor for chronic rejection, a relentlessly progressive process. As the occurrence of acute rejection episodes is the most powerful predictive factor for the later development of chronic rejection in adults and children, strategies to detect and ablate acute rejection episodes as early as possible would help mitigate these occurrences. However, current monitoring and diagnostic modalities may be ill-suited to the diagnosis of acute rejection at an early stage.

For example, acute renal allograft rejection is currently diagnosed following percutaneous needle core biopsy of the allograft. The invasive biopsy procedure, in most instances, is performed following an increase in serum creatinine. Whereas increased serum creatinine levels are currently the best surrogate markers of acute rejection, they lack sensitivity and specificity with respect to predicting rejection.

Procedures to diagnose allograft rejection generally depend upon detection of graft dysfunction and the presence of a mononuclear leukocytic infiltrate. However, the presence of a modest cellular infiltrate is often not conclusive and can be detected in non-rejecting grafts. It would be helpful to have a reliable tool for diagnosis and follow-up of acute allograft rejection.

Accordingly, a need exists for identifying gene- or protein-based tests that are more sensitive and which can be used in clinical diagnosis of rejection, especially in its early and/or pre-clinical state.

SUMMARY

Described herein for the first time is an analysis of genes that are up-regulated simultaneously, and which provide a "molecular signature" to accurately detect transplant rejection. Early diagnosis of allograft rejection (e.g., renal allograft rejection) and new prognostic markers are important to minimize and personalize immunosuppression. In addition to histopathological differential diagnosis, gene expression profiling significantly improves disease classification by defining these molecular signatures.

Methods and compositions for monitoring the status of a transplanted organ in a subject are described herein. This involves evaluating transplant rejection in a subject by determining the magnitude of gene expression in a post-transplant sample obtained from the subject and comparing the relative expression of the marker genes to a baseline level of the marker. Up-regulation of gene expression (i.e., increased or decreased gene expression) of a plurality of selected genes in the sample indicates rejection. Increased expression of the combination of the genes in Table 3, indicates transplant rejection. In another embodiment, increased expression of one, two or more genes of any of the genes of Table 3, indicates transplant rejection.

Accordingly, in one aspect, the invention pertains to a method for assessing the onset of rejection of a transplanted organ in a subject, by obtaining a post-transplantation sample from the subject. The level of gene expression in the post-transplantation sample of a plurality of genes shown in Table 3 is determined, with at least one gene being associated with the NADPH oxidase pathway. The magnitude of gene expression of the at least one gene in the post-transplantation sample is compared with the magnitude of gene expression of the same gene in a control sample. Our control includes biopsies from non transplanted healthy kidney or from transplanted kidney showing no sign of rejection]. The up-regulation of at least one gene indicates that the subject is likely to experience transplant rejection, thereby assessing the onset of rejection of the transplanted organ in the subject.

The method can be used to assess acute transplant rejection, and in particular, early acute transplant rejection. The up-regulation of the plurality of genes in Table 3 provides a molecular signature which indicates that the subject is likely to experience acute transplant rejection. The magnitude of expression in the sample can be determined quantitatively. A magnitude of expression of the plurality of genes in the sample that differs from the control sample magnitude of expression by a factor of at least about 2 or about 3, indicates that the subject is likely to experience acute transplant rejection.

The invention also relates to measuring clusters of genes according to biological/physiological function whose expression levels are indicative of transplant rejection. This is accomplished by measuring the up-regulation of the expression of at least two genes selected from one or more gene clusters in a post-transplantation test sample wherein up-regulated gene expression of at least two of said genes indicates acute transplant rejection. The invention provides several gene clusters including, but not limited to, the hematopoiesis cluster, the B lymphocyte cluster, the T lymphocyte cluster, the lysosome cluster, the immunoproteasome cluster, the NADPH oxidase pathway cluster, the IFN gamma pathway cluster, the apoptosis cluster, and the integrin and extracellular matrix cluster. In this aspect of the invention, there preferably about 75% consistency of up-regulated genes from different patients, more preferably about 80% consistency, about 85% consistency, about 90%, about 95% consistency, and even more preferably, about 96%, 97%, 98%, 99% and 100% consistency of up-regulated genes.

Accordingly, in another aspect, the invention pertains to a method for assessing the onset of rejection of a transplanted organ in a subject by obtaining a post-transplantation sample from the subject. The magnitude of gene expression is determined in the post-transplantation sample of a combination of a plurality of genes selected from the group consisting of a gene associated with hematopoiesis, a gene associated with B lymphocytes, a gene associated with T lymphocytes, a gene associated with a lysosome, a gene associated with MHC, a gene associated with an immunoproteasome, a gene associated with an NADPH oxidase pathway, a gene associated with an IFN gamma pathway, a gene associated with apoptosis, and a gene associated with integrin and an extracellular matrix. The magnitude of gene expression of the combination of genes in the post-transplantation sample with the magnitude of gene expression of the same combination of genes in a control sample can be compared. Up-regulation of the combination of genes indicates that the subject is likely to experience transplant rejection, thereby assessing the onset of rejection of the transplanted organ in the subject.

The gene associated with hematopoiesis can be selected from the group consisting of CD18 (NM_000211), CD44 (NM_001001389; NM_000610), CD44 (NM_001001390; NM_001001391), CD52 (NM_001803), CD53 (NM_000560), hematopoietic cell-specific Lyn substrate 1 (NM_005335), hematopoietic cell kinase (NM_002110).

The gene associated with B lymphocytes can be selected from the group consisting of IgM (BC089412), IgM heavy chain (XM_522973), CD48 antigen (NM_001778), hypothetical protein MGC27165 (IgA) (S55735), similar to PKC beta 1 (BM684568), protein kinase C beta 1 (NM_002738), and protein kinase C beta 1 (X06318).

The gene associated with T lymphocytes can be selected from the group consisting of CD8 antigen alpha polypeptide (NM_171827; NM_001768), interleukin 10 receptor alpha (NM_001558), lymphocyte cystolic protein 1 (L-plastin) (NM_002298), lymphocyte-specific protein tyrosine kinase (NM_005356), protein kinase C beta 1 (X06318), protein kinase C beta 1 (NM_002738), Rac2 (NM_002872), Rho GDP dissociation inhibitor (GDI) beta (NM_001175), similar to PKC beta 1 (BM684568), SLP76 (NM_005565), Src-like-adaptor (NM_006748), and STAT1 (NM_139266).

The gene associated with a lysosome can be selected from the group consisting of lysosomal-associated multispanning membrane protein-5 (NM_006762), lysozyme (NM_000239), and pleckstrin (NM_002664).

The gene associated with MHC can be selected from the group consisting of MHC class I B (NM_005514), MHC class I C(NM_002117), MHC class II DM beta (NM_002118), MHC class II DP beta 1 (NM_002121), MHC class II DQ beta 1 (NM_002123), MHC class II DR alpha (NM_019111), MHC class II DR beta 3 (NM_022555; NM_021983), MHC class II DR beta 3 (NM_002124, NM_002125), and MHC class II DM alpha (NM_006120).

The gene associated with an immunoproteasome can be selected from the group consisting of proteasome subunit beta type 8 (NM_004159; NM_148919), proteasome subunit beta type 9 (NM_002800; NM_148954), proteasome subunit beta type 10 (NM_002801), TAP1 (NM_000593), and ubiquitin D (NM_006398).

The gene associated with an NADPH oxidase pathway can be selected from the group consisting of cytochrome b-245 beta polypeptide (NM_000397), pleckstrin (NM_002664), rac2 (NM_002872) and Rho GDP dissociation inhibitor (GDI) beta (NM_001175).

The gene associated with an IFN gamma pathway can be selected from the group consisting of chemokine ligand 5 (NM_002985), chemokine ligand 10 (NM_001565), chemokine ligand 9 (NM_002416), GBP1 (NM_002053), GBP2 (AL832451), granzyme A (NM_006144), interferon stimulated gene 20 kDa (ISG20) (NM_002201), proteasome subunit beta type 10 (202659), proteasome subunit beta type 8 (NM_004159; NM_148919), proteasome subunit beta type 9 (NM_002800; NM_148954), STAT1 (NM_139266), TAP1 (NM_000593), and ubiquitin D (NM_006398).

The gene associated with apoptosis can be selected from the group consisting of caspase 1 (NM_001223), caspase 1 (NM_033292), caspase 1 (NM_033293), caspase 1 (NM_033294, NM_033295), CD27 (NM_001242), granzyme A (NM_006144), proteoglycan 1 (NM_002727), similar to TRAF3-interacting JNK-activating modulator (NM_025228), and TRAF3-interacting JNK-activating modulator (XM_514166).

The gene associated with integrin and an extracellular matrix can be selected from the group consisting of CD18 (NM_000211), CD44 (NM_001001389; NM_000610), CD44 (NM_001001390; NM_001001391), chondroitin sulfate proteoglycan 2 (NM_004385), glia maturation factor gamma (NM_004877), MMP7 (NM_002423), Rac2 (NM_002872), Rho GDP dissociation inhibitor (GDI) beta (NM_001175), runt-related transcription factor 3 (NM_004350), tenascin C (NM_002160), tenascin C (AL162425), and TIMP1 (NM_003254).

Thus, as a result of the work described herein, methods are now available to accurately quantitate marker gene expression in biopsy tissue, urine, peripheral blood mononuclear cells and other body fluids, and to correlate the magnitude of expression of these genes with rejection of allografts.

In another aspect, the invention pertains to a method of monitoring transplant rejection in a subject by taking as a baseline value the magnitude of gene expression of a combination of a plurality of genes in a sample obtained from a transplanted subject who is known not to develop rejection. The magnitude of gene expression corresponding to the combination of a plurality of genes is detected in a sample obtained from the subject post-transplantation. The first value is compared with the second value, wherein a first value lower or higher than the second value predicts that the transplanted subject is at risk of developing rejection, wherein the plurality of genes are defined in Table 3.

In another aspect, the invention pertains to a method of monitoring transplant rejection in a subject detecting a magnitude of gene expression corresponding to a combination of a plurality of genes from a sample obtained from a donor subject at the day of transplantation. The magnitude of gene expression corresponding to the plurality of genes is detected from a sample obtained from a recipient subject post-transplantation. The first value is compared with the second value, wherein a first value lower or higher than the second value predicts that the recipient subject is at risk of developing rejection; wherein the plurality of genes are as defined in Table 3.

In another aspect, the invention pertains a method for monitoring transplant rejection in a subject at risk thereof by obtaining a pre-administration sample from a transplanted subject prior to administration of a rejection inhibiting agent. The magnitude of gene expression of a plurality of genes is detected in the pre-administration sample. One or more post-administration samples are obtained from the transplanted subject and the magnitude of gene expression of a plurality of genes is detected in the post-administration sample or samples. The magnitude of gene expression of the plurality of genes in the pre-administration sample is compared with the magnitude of gene expression in the post-administration sample or samples, and the agent is adjusted accordingly, wherein the plurality of genes are defined in Table 3.

In another aspect, the invention pertains to a method for preventing, inhibiting, reducing or treating transplant rejection in a subject in need of such treatment comprising administering to the subject a compound that modulates the synthesis, expression or activity of one or more genes or gene products encoded thereof of genes as identified in Table 3, so that at least one symptom of rejection is ameliorated.

In another aspect, the invention pertains to a method for identifying agents for use in the prevention, inhibition, reduction or treatment of transplant rejection comprising monitoring the level of gene expression of one or more genes or gene products as identified in Table 3. The magnitude of gene expression can be assessed by detecting the presence of a protein encoded by the gene, for example by a reagent which specifically binds to the protein.

Detecting the combination of the plurality of genes or expression products thereof as listed in Table 3 can be used as a biomarker for transplant rejection. Compound which modulate the synthesis, expression of activity of one or more genes as identified in Table 3, or an expression product thereof, can also be used for the preparation of a medicament for prevention or treatment of transplant rejection in a subject.

In another aspect, the invention pertains to a method of monitoring transplant rejection in a subject by taking as a baseline value the magnitude of gene expression corresponding to a combination of a plurality of genes in a sample of a transplanted subject who is known not to develop rejection.

The magnitude of gene expression corresponding to the combination of the plurality of genes can be compared to the magnitude of gene expression in a sample obtained from a subject post-transplantation. The first value can be compared with the second value, wherein a first value lower or higher than the second value predicts that the transplanted subject is at risk of developing rejection, wherein the plurality of genes are as defined in Table 3.

DETAILED DESCRIPTION

Figure 1:
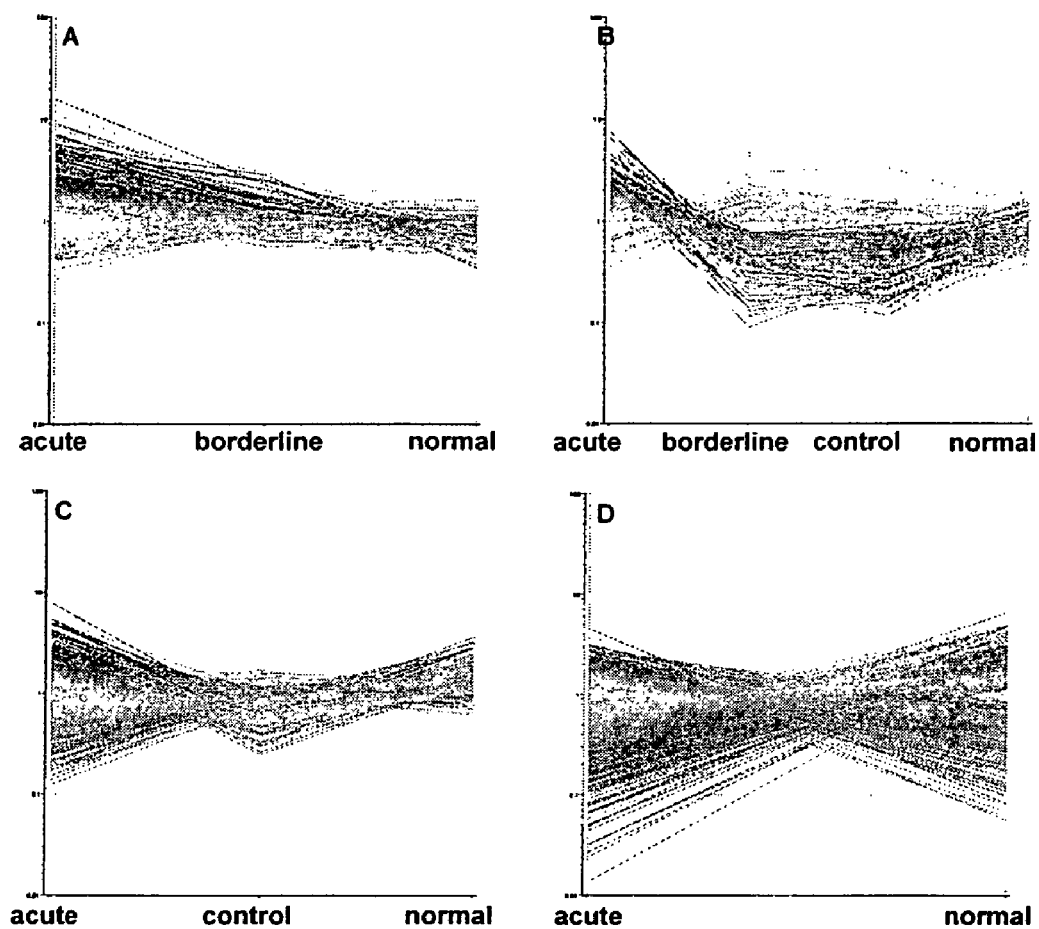
FIG. 1 depicts the gene expression profile of genes from 4 independent Affymetrix datasets used in the meta-analysis.

The invention is based, in part, on the discovery that a select combination of genes are up-regulated in acute rejection. Early diagnosis of renal allograft rejection and new prognostic markers are important minimize and personalize immunosuppression. In addition to histopathological differential diagnosis, gene expression profiling significantly improves disease classification by defining a "molecular signature." Several previous studies have successfully applied a transcriptomic approach to distinguish different classes of kidney transplants. However, the heterogeneity of microarray platforms and various data analysis methods complicates the identification of robust signatures of acute rejection. To address this issue, a comparative meta-analysis was performed which identifies the intersection of multiple gene expression signatures from different microarray datasets. The strong association between the up-regulation of combination of genes disclosed in Table 3 provides a "molecular signature" for a transplant rejection, in particular acute rejection.

To further facilitate an understanding of the present invention, a number of terms and phrases are defined below:

The term "transplantation" as used herein refers to the process of taking a cell, tissue, or organ, called a "transplant" or "graft" from one subject and placing it or them into a (usually) different subject. The subject who provides the transplant is called the "donor" and the subject who received the transplant is called the "recipient". An organ, or graft, transplanted between two genetically different subject s of the same species is called an "allograft". A graft transplanted between subjects of different species is called a "xenograft".

The term "transplant rejection" as used herein is defined as functional and structural deterioration of the organ due to an active immune response expressed by the recipient, and independent of non-immunologic causes of organ dysfunction.

The term "acute rejection" as used herein refers to a rejection of the transplanted organ developing after the first 5-60 post-transplant days. It is generally a manifestation of cell-mediated immune injury. It is believed that both delayed hypersensitivity and cytotoxicity mechanisms are involved. The immune injury is directed against HLA, and possibly other cell-specific antigens expressed by the tubular epithelium and vascular endothelium.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" includes an amino acid (e.g., peptide or polypeptide) generated when a gene is transcribed and translated.

The term "magnitude of expression" as used herein refers to quantifying marker gene transcripts and comparing this quantity to the quantity of transcripts of a constitutively expressed gene. The term "magnitude of expression" means a "normalized, or standardized amount of gene expression". For example, the overall expression of all genes in cells varies (i.e., is not constant). To accurately assess whether the detection of increased mRNA transcript is significant, it is preferable to "normalize" gene expression to accurately compare levels of expression between samples, i.e., it is a baselevel against which gene expression is compared. In one embodiment, the expressed gene is associated with the NADPH oxidase pathway. Quantification of gene transcripts was accomplished using competitive reverse transcription polymerase chain reaction (RT-PCR) and the magnitude of gene expression was determined by calculating the ratio of the quantity of gene expression of each marker gene to the quantity of gene expression of the expressed gene.

The term "differentially expressed", as applied to a gene, includes the differential production of mRNA transcribed from a gene or a protein product encoded by the gene. A differentially expressed gene may be overexpressed or underexpressed as compared to the expression level of a normal or control cell. In one aspect, it includes a differential that is at least 2 times, at least 3 times, at least 4 times, at least 5 times, at least 6 times, at least 7 times, at least 8 times, at least 9 times or at least 10 times higher or lower than the expression level detected in a control sample. In a preferred embodiment, the expression is higher than the control sample. The term "differentially expressed" also includes nucleotide sequences in a cell or tissue which are expressed where silent in a control cell or not expressed where expressed in a control cell.

The term "sample" as used herein refers to cells obtained from a biopsy. The term "sample" also refers to cells obtained from a fluid sample including, but not limited to, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A fluid test sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. A "post-transplantation fluid test sample" refers to a sample obtained from a subject after the transplantation has been performed.

Sequential samples can also be obtained from the subject and the quantification of immune activation gene markers determined as described herein, and the course of rejection can be followed over a period of time. In this case, for example, the baseline magnitude of gene expression of the immune activation marker genes is the magnitude of gene expression in a post-transplant sample taken after the transplant. For example, an initial sample or samples can be taken within the nonrejection period, for example, within one week of transplantation and the magnitude of expression of marker genes in these samples can be compared with the magnitude of expression of the genes in samples taken after one week. In one embodiment, the samples are taken on weeks 6, 12 and 24 post-transplantation The term "biopsy" as used herein refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. In one embodiment, a fine needle aspiration biopsy is used. In another embodiment, a minicore needle biopsy is used. A conventional percutaneous core needle biopsy can also be used.

The term "up-regulation" or "up-regulated" are used interchangeably herein and refer to the increase or elevation in the amount of a target gene or a target protein. The term "up-regulation" or "up-regulated" also refers to the increase or elevation of processes or signal transduction cascades involving a target gene or a target protein.

The term "gene cluster" or "cluster" as used herein refers to a group of genes related by expression pattern. In other words, a cluster of genes is a group of genes with similar regulation across different conditions, such as graft nonrejection versus graft rejection. The expression profile for each gene in a cluster should be correlated with the expression profile of at least one other gene in that cluster. Correlation may be evaluated using a variety of statistical methods. Often, but not always, members of a gene cluster have similar biological functions in addition to similar gene expression patterns.

A "hematopoiesis gene cluster" is the cluster of genes grouped according to the biological/physiological function of cells involved in hematopoiesis, as exemplified by CD18, CD44, CD44, CD52, CD53, hematopoietic cell-specific Lyn substrate 1, hematopoietic cell kinase, and similar CD52 Members of this gene cluster have expression patterns in rejection versus non-rejection transplant samples that are substantially related to the expression patterns for these genes.

A "B-lymphocyte gene cluster" is the cluster of genes grouped according to the biological/physiological function of B-lymphocyte cells, as exemplified by IgM, IgM heavy chain, CD48 antigen hypothetical protein MGC27165 (IgA), similar to PKC beta 1, protein kinase C beta 1, and protein kinase C beta L Members of this gene cluster have expression patterns in rejection versus non-rejection transplant samples that are substantially related to the expression patterns for these genes.

A "T-lymphocyte gene cluster" is the cluster of genes grouped according to the biological/physiological function of T-cells, as exemplified by CD8 antigen alpha polypeptide, interleukin 10 receptor alpha, lymphocyte cystolic protein 1 (L-plastin), lymphocyte-specific protein tyrosine kinase, lymphocyte-specific protein tyrosine kinase, protein kinase C beta 1, protein kinase C beta 1, Rac2, Rho GDP dissociation inhibitor (GDI) beta, similar to PKC beta 1, SLP76, Src-like-adaptor, Src-like-adaptor, and STAT1. Members of this gene cluster have expression patterns in rejection versus non-rejection transplant samples that are substantially related to the expression patterns for these genes.

A "lysosome gene cluster" is the cluster of genes grouped according to the biological/physiological function of lysosome cells, as exemplified by lysosomal-associated multi-spanning membrane protein-5, lysosomal-associated multi-spanning membrane protein-5, lysozyme, and pleckstrin. Members of this gene cluster have expression patterns in rejection versus non-rejection transplant samples that are substantially related to the expression patterns for these genes.

A "MHC gene cluster" is the cluster of genes grouped according to the biological/physiological function of MHC cells, as exemplified by MHC class I B, MHC class I C, MHC class II DM beta, MHC class II DP beta 1, MHC class II DQ beta 1, MHC class II DQ beta 1, MHC class II DQ beta 2, MHC class II DR alpha, MHC class II DR alpha, MHC class II DR beta 3, MHC class II DR beta 3, and MHC class II DM alpha Members of this gene cluster have expression patterns in rejection versus non-rejection transplant samples that are substantially related to the expression patterns for these genes.

A "immunoproteasome gene cluster" is the cluster of genes grouped according to the biological/physiological function of immunoproteasome cells, as exemplified by proteasome subunit beta type 8, proteasome subunit beta type 9, proteasome subunit beta type 10, TAP1, and ubiquitin D. Members of this gene cluster have expression patterns in rejection versus non-rejection transplant samples that are substantially related to the expression patterns for these genes.

An "NADPH oxidase pathway gene cluster" is the cluster of genes grouped according to the biological/physiological function of cells involved in the NADPH oxidase pathway, as exemplified by cytochrome b-245 beta polypeptide, pleckstrin, rac2 and Rho GDP dissociation inhibitor (GDI) beta. Members of this gene cluster have expression patterns in rejection versus non-rejection transplant samples that are substantially related to the expression patterns for these genes.

An "IFN gamma pathway gene cluster" is the cluster of genes grouped according to the biological/physiological function of cells involved in the IFN gamma pathway, as exemplified by a chemokine ligand 5, chemokine ligand 5, chemokine ligand 10, chemokine ligand 9, GBP1, GBP1, GBP2, granzyme A, interferon stimulated gene 20 kDa (ISG20), similar to ISG 20, proteasome subunit beta type 10, proteasome subunit beta type 8, proteasome subunit beta type 9, STAT1, TAP1, and ubiquitin D. Members of this gene cluster have expression patterns in rejection versus non-rejection transplant samples that are substantially related to the expression patterns for these genes.

An "apoptosis gene cluster" is the cluster of genes grouped according to the biological/physiological function of cells involved in apoptosis, as exemplified by caspase 1, CD27, granzyme A, proteoglycan 1, similar to TRAF3-interacting JNK-activating modulator, and TRAF3-interacting JNK-activating modulator. Members of this gene cluster have expression patterns in rejection versus non-rejection transplant samples that are substantially related to the expression patterns for these genes.

An "integrin and an extracellular matrix gene cluster" is the cluster of genes grouped according to the biological/physiological function of cells involved with integrin and extracellular matrix, as exemplified by CD 18, CD44, chondroitin sulfate proteoglycan 2, glia maturation factor gamma, MMP7, Rac2, Rho GDP dissociation inhibitor (GDI) beta, runt-related transcription factor 3, runt-related transcription factor 3, tenascin C, tenascin C, and TIMP1. Members of this gene cluster have expression patterns in rejection versus non-rejection transplant samples that are substantially related to the expression patterns for these genes.

A "probe set" as used herein refers to a group of nucleic acids that may be used to detect two or more genes. Detection may be, for example, through amplification as in PCR and RT-PCR, or through hybridization, as on a microarray, or through selective destruction and protection, as in assays based on the selective enzymatic degradation of single or double stranded nucleic acids. Probes in a probe set may be labeled with one or more fluorescent, radioactive or other detectable moieties (including enzymes). Probes may be any size so long as the probe is sufficiently large to selectively detect the desired gene. A probe set may be in solution, as would be typical for multiplex PCR, or a probe set may be adhered to a solid surface, as in an array or microarray. It is well known that compounds such as PNAs may be used instead of nucleic acids to hybridize to genes. In addition, probes may contain rare or unnatural nucleic acids such as inosine.

The terms "polynucleotide" and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for guanine when the polynucleotide is RNA. This, the term "polynucleotide sequence" is the alphabetical representation of a polynucleotide molecule. This alphabetical representation can be inputted into databases in a computer having a central processing unit and used for bioinformatics applications such as functional genomics and homology searching.

The term "cDNAs" includes complementary DNA, that is mRNA molecules present in a cell or organism made into cDNA with an enzyme such as reverse transcriptase. A "cDNA library" includes a collection of mRNA molecules present in a cell or organism, converted into cDNA molecules with the enzyme reverse transcriptase, then inserted into "vectors" (other DNA molecules that can continue to replicate after addition of foreign DNA). Exemplary vectors for libraries include bacteriophage, viruses that infect bacteria (e.g., lambda phage). The library can then be probed for the specific cDNA (and thus mRNA) of interest.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are well known in the art, and are taught, for example, in MacPherson et al., IRL Press at Oxford University Press (1991)). All processes of producing replicate copies of a polynucleotide, such as PCR or gene cloning, are collectively referred to herein as "replication". A primer can also be used as a probe in hybridization reactions, such as Southern or Northern blot analyses (see, e.g., Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

The term "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6.times.sodium chloride/sodium citrate (SSC) at about 45.degree. C., followed by one or more washes in 0.2.times.SSC, 0.1% SDS at 50.degree. C., preferably at 55.degree. C., more preferably at 60.degree. C., and even more preferably at 65.degree. C.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementary" or "homology" (the degree that one polynucleotide is complementary with another) is quantifiable in terms of the proportion of bases in opposing strands that are expected to hydrogen bond with each other, according to generally accepted base-pairing rules.

As used herein, the term "marker" includes a polynucleotide or polypeptide molecule which is present or increased in quantity or activity in subjects at risk for organ rejection. The relative change in quantity or activity of the marker is correlated with the incidence or risk of incidence of rejection.

As used herein, the term "panel of markers" includes a group of markers, the quantity or activity of each member of which is correlated with the incidence or risk of incidence of organ rejection. In certain embodiments, a panel of markers may include only those markers which are either increased in quantity or activity in subjects at risk for organ rejection.

I. Transplant Rejection

The present invention relates to the identification of genes, which are up-regulated during rejection, in particular during early acute rejection. A highly statistically significant correlation has been found between the expression of a combination of gene and acute rejection, thereby providing a "molecular signature" for transplant rejection (e.g., acute renal rejection, in particular early acute renal rejection). By virtue of the co-expression of these genes organs that are likely to undergo rejection, these genes and their expression products can be used in the management, prognosis and treatment of patients at risk of transplant rejection.

Accordingly, in one aspect the invention pertains to using a recognition signature comprising a combination of genes shown in Table 3 to indicate transplant rejection, in particular acute rejection of a transplanted organ.

The single most common cause for early graft failure, especially within one month post-transplantation, is immunologic rejection of the allograft. The unfavorable impact of the rejection is magnified by the fact that: (a) the use of high-dose anti-rejection therapy, superimposed upon maintenance immunosuppression, is primarily responsible for the morbidity and mortality associated with transplantation, (b) the immunization against "public" HLA-specificities resulting from a rejected graft renders this patient population difficult to retransplant and (c) the return of the immunized recipient with a failed graft to the pool of patients awaiting transplantation enhances the perennial problem of organ shortage.

Antigen-triggered T-cell activation and the subsequent infiltration of activated CD4+ and CD8+ T-cell clones, macrophages, and natural killer (NK) cells into the graft are key events of acute allograft rejection. However a biopsy result indicating T-cell invasion into a transplant is not sufficient for a confident diagnosis. For example, although a T-cell-rich interstitial nephritis is a hallmark of acute renal allograft rejection, clinical rejection episodes responsive to treatment often show only a modest cellular infiltrate and similar infiltrates are observed in surveillance biopsies obtained in well-functioning renal allografts (Rush et al., Transplantation 57: 208-211 (1994)); (Rush et al., Transplantation 59: 511-514 (1994)).

The differentiation of the diagnosis of rejection from other etiologies for graft dysfunction and institution of effective therapy is further complicated because: (a) the percutaneous core needle biopsy of grafts, the best of available current tools to diagnose rejection is performed usually after the "fact", i.e., graft dysfunction and graft damage (irreversible in some instances) are already present, (b) the morphological analysis of the graft provides modest clues with respect to the potential for reversal of a given rejection episode, and minimal clues regarding the likelihood of recurrence ("rebound"), and (c) the mechanistic basis of the rejection phenomenon, a prerequisite for the design of therapeutic strategies, is poorly defined by current diagnostic indices, including morphologic features of rejection.

The diagnosis of, for example, renal allograft rejection is made usually by the development of graft dysfunction (e.g., an increase in the concentration of serum creatinine) and morphologic evidence of graft injury in areas of the graft also manifesting mononuclear cell infiltration. Two caveats apply, however, to the use of abnormal renal function as an indicator of the rejection process: first, deterioration in renal function is not always available as a clinical clue to diagnose rejection since many of the cadaveric renal grafts suffer from acute (reversible) renal failure in the immediate post-transplantation period due to injury from harvesting and ex-vivo preservation procedures. Second, even when immediately unimpaired renal function is present, graft dysfunction might develop due to a non-immunologic cause, such as immunosuppressive therapy itself.

For example, cyclosporine (CsA) nephrotoxicity, a complication that is not readily identified solely on the basis of plasma/blood concentrations of CsA, is a common complication. The clinical importance of distinguishing rejection from CsA nephrotoxicity cannot be overemphasized since the therapeutic strategies are diametrically opposite: escalation of immunosuppressants for rejection, and reduction of CsA dosage for nephrotoxicity.

The invention is based, in part, on the observation that increased or decreased expression of many different genes and/or the encoded proteins is associated with certain graft rejection states. As a result of the data described herein, methods are now available for the rapid and reliable diagnosis of acute and chronic rejection, even in cases where allograft biopsies show only mild cellular infiltrates. Described herein for the first time is an analysis of genes that are up-regulated simultaneously and which provide a molecular signature to accurately detect transplant rejection.

In addition, the invention is partly based on the observation that genes are expressed as gene clusters—groups of genes, often functionally related, that have substantially related expression profiles under certain circumstances. Accordingly, the invention provides clusters of genes, the expression of the members of which is correlated with graft rejection. The invention further provides classic molecular methods and large scale methods for measuring expression of suitable marker genes.

The methods described herein are particularly useful for detecting acute transplant rejection and preferably early acute transplant rejection. Most typically, the subject (i.e., the recipient of a transplant) is a mammal, such as a human. The transplanted organ can include any transplantable organ or tissue, for example kidney, heart, lung, liver, pancreas, bone, bone marrow, bowel, nerve, stem cells (or stem cell-derived cells), tissue component and tissue composite. In a preferred embodiment, the transplant is a kidney transplant.

The methods described herein are useful to assess the efficacy of anti-rejection therapy. Such methods involve comparing the pro-administration magnitude of the transcripts of the marker genes to the post-administration magnitude of the transcripts of the same genes, where a post-administration magnitude of the transcripts of the genes that is less than the pre-administration magnitude of the transcripts of the same genes indicates the efficacy of the anti-rejection therapy. Any candidates for prevention and/or treatment of transplant rejection, (such as drugs, antibodies, or other forms of rejection or prevention) can be screened by comparison of magnitude of marker expression before and after exposure to the candidate. In addition, valuable information can be gathered in this manner to aid in the determination of future clinical management of the subject upon whose biological material the assessment is being performed. The assessment can be performed using a sample from the subject, using the methods described herein for determining the magnitude of gene expression of the marker genes. Analysis can further comprise detection of an infectious agent.

II. Gene Combinations and Gene Clusters

In another aspect, the invention relates to the discovery of gene clusters that are diagnostic of acute transplant rejection and gene clusters that are diagnostic of other transplant-related conditions (see Table 1). Advances in highly parallel, automated DNA hybridization techniques combined with the growing wealth of human gene sequence information have made it feasible to simultaneously analyze expression levels for thousands of genes (see, e.g., Schena et al., 1995, Science 270:467-470; Lockhort et al., 1996, Nature Biotechnology 14:1675-1680; Blanchard et al., 1996, Nature Biotechnology 14:1649; Ashby et al., U.S. Pat. No. 5,569,588, issued Oct. 29, 1996; Perou et al., 2000, Nature 406:747-752;). Methods such as the gene-by-gene quantitative RT-PCR described in the Examples are highly accurate but relatively labor intensive. While it is possible to analyze the expression of thousands of genes using quantitative PCR, the effort and expense would be enormous. Instead, as an example of large scale analysis, an entire population of mRNAs may be converted to cDNA and hybridized to an ordered array of probes that represent anywhere from ten to ten thousand or more genes. The relative amount of cDNA that hybridizes to each of these probes is a measure of the expression level of the corresponding gene. The data may then be statistically analyzed to reveal informative patterns of gene expression.

The advent of large scale gene expression analysis has revealed that groups of genes are often expressed together in a coordinated manner. For example, whole genome expression analysis in the yeast *Saccharomyces cerevisiae* showed coordinate regulation of metabolic genes during a change in growth conditions known as the diauxic shift (DiRisi et al., 1997, Science 278:680-686; Eisen et al., 1998, PNAS 95:14863-14868). The diauxic shift occurs when yeast cells fermenting glucose to ethanol exhaust the glucose in the media and begin to metabolize the ethanol. In the presence of glucose, genes of the glycolytic pathway are expressed and carry out the fermentation of glucose to ethanol. When the glucose is exhausted, yeast cells must metabolize the ethanol, a process that depends heavily on the Krebs cycle and respiration.

Accordingly, the expression of glycolysis genes decreases, and the expression of Krebs cycle and respiratory genes increases in a coordinate manner. Similar coordinate gene regulation has been found in various cancer cells. Genes encoding proteins involved in cell cycle progression and DNA synthesis are often coordinately overexpressed in cancerous cells (Ross et al., 2000, Nature Genet. 24:227-235; Perou et al., 1999, PNAS 96:9212-9217; Perou et al., 2000, Nature 406:747-752).

The coordinate regulation of genes is logical from a functional point of view. Most cellular processes require multiple genes, for example: glycolysis, the Krebs cycle, and cell cycle progression are all multi-gene processes. Coordinate expression of functionally related genes is therefore essential to permit cells to perform various cellular activities. Such groupings of genes can be called "gene clusters" (Eisen et al., 1998, PNAS 95:14863-68).

Clustering of gene expression is not only a functional necessity, but also a natural consequence of the mechanisms of transcriptional control. Gene expression is regulated primarily by transcriptional regulators that bind to cis-acting DNA sequences, also called regulatory elements. The pattern of expression for a particular gene is the result of the sum of the activities of the various transcriptional regulators that act on that gene. Therefore, genes that have a similar set of regulatory elements will also have a similar expression pattern and will tend to cluster together. Of course, it is also possible, and quite common, for genes that have different regulatory elements to be expressed coordinately under certain circumstances.

In one exemplary embodiment, transplant rejection state may be diagnosed by detecting up-regulation or a plurality of genes from a combination of gene clusters. Thus, the method involves determining the magnitude of a plurality of genes selected from one or more gene clusters selected from the group consisting of the hematopoiesis gene cluster, the B lymphocyte gene cluster, the T lymphocyte gene cluster, the lysosome gene cluster, the MHC gene cluster, the immunoproteasome gene cluster, the NADPH oxidase pathway gene cluster, the IFN gamma pathway gene cluster, the apoptosis gene cluster, and the integrin and an extracellular matrix gene cluster. These methods, involving determining the magnitude a plurality of genes selected from one or more gene clusters selected from the group consisting of the hematopoiesis gene cluster, the B lymphocyte gene cluster, the T lymphocyte gene cluster, the lysosome gene cluster, the MHC gene cluster, the immunoproteasom gene cluster, the NADPH oxidase pathway gene cluster, the IFN gamma pathway gene cluster, the apoptosis gene cluster, and the integrin and an extracellular matrix gene cluster are also applicable to the treatment of other transplant related conditions not involving rejection, as will be appreciated by those of skill in the art.

In T-cell-mediated acute rejection, the graft is infiltrated by effector T cells, activated macrophages, B cells, and plasma cells and displays IFN-gamma effects, increased chemokine expression and extracellular matrix, altered capillary permeability and deterioration of parenchymal function The diagnostic lesions of T-cell-mediated rejection reflect mononuclear cells invading the kidney tubules (tubulitis) and the intima of small arteries (arteritis). Macrophages, activated by T cells, participate in the development of the inflammatory response by secreting a large variety of biologically active molecules, but the injury remains antigen-specific. Injury is mainly associated with cytotoxic T cell induced lysis of target cells in the kidney, but may also involve parenchymal transdifferentiation into mesenchymal cells and cell senescence.

The vast majority of the 81 gene probes and 57 selected genes reflect the major biological events occurring during the ongoing immune and inflammatory response observed in allograft rejection. These genes can be directly associated with recruitment and activation of B cells, T cells and antigen presenting cells (APCs) in the transplanted kidney. In this meta-analysis, robust signatures for chemokines, integrin or extracellular matrix pathways as well as IF N-gamma related effects, cytotoxicity and apoptose, were identified General Hematopoietic Markers The following genes are specifically expressed in hematopoietic cells, mainly in B and T lymphocytes, NK cells and APC (monocytes and macrophages). Therefore, these signatures are general markers for hematopoietic cells infiltration into the kidney.

| Affymetrix Ids | Accession Number | Gene name | Gene symbol |
|---|---|---|---|
| 1557905_s_at | NM_001001389 NM_000610 | CD44 antigen, transcript variant 1 and 2, mRNA. | CD44 |
| 212063_at | NM_001001390 NM_001001391 | CD44 antigen, transcript variant 3 and 4, mRNA. | CD44 |
| 204661_at | NM_001803 | CD52 antigen | CD52 |
| 34210_at | NM_001803 | CD52 antigen | CD52 |
| 203416_at | NM_000560 | CD53 antigen | CD53 |
| 242946_at | AL391064 | CD53 antigen | CD53 |
| 202957_at | NM_005335 | hematopoietic cell-specific Lyn substrate 1 | HCLS1 |
| 208018_s_at | NM_002110 | hemopoietic cell kinase | HCK |
| 202803_s_at | NM_000211 | integrin, beta 2 | ITGB2 |
| 1555349_a_at | NM_000211 | integrin, beta 2 | ITGB2 |

B Lymphocytes Markers

One of the most surprising result from Sarwal et al. was the description of the strong association between B cell infiltration and the clinical phenotype of glucocorticoid resistance among patients in AR type I group, leading to poorer functional recovery (4). Through this meta analysis, we confirmed that specific B cell markers were a prominent features of early AR but were also observed as very heterogenous markers. The following signatures specifically sign the B cell infiltration into the kidney.

| Affymetrix Ids | Accession Number | Gene name | Gene symbol |
|---|---|---|---|
| 212827_at | BC089412 | similar to IgM heavy chain | IGHM |
| 217022_s_at | S55735 | immunoglobulin alpha1 heavy chain | IGHA1 |
| 209374_s_at | XM_522973 | immunoglobulin heavy constant mu | IGHM |
| 204118_at | NM_001778 | CD48 antigen | CD48 |
| 207957_s_at | X06318 | protein kinase C, beta 1 | PRKCB1 |
| 209685_s_at | NM_002738 | protein kinase C, beta 1, transcript variant 2 | PRKCB1 |
| 227817_at | BM684568 | similar to PKC beta 1 | PRKCB1 |

T Cell Infiltration and Activation

T cell response to donor alloantigen is the key feature of organ acute rejection. Full activation of the T cell requires the delivery of two separate but complementary signals. Signal 1 is delivered during the cognate interaction between the T cell receptor (TCR/CD3 complex and the MHC-bound peptide on an antigen presenting cell (APC). The second signal is an antigen non specific 'positive' signal triggered by the interaction of a pair of costimulatory molecules expressed in T cell and APC. As such, co-stimulatory molecules do not trigger T cell activation alone but rather augment signal 1 delivered by the TCR. Consistent with the pathophysiology of allograft rejection, signature for T cell specific and TCR signaling pathways are highly represented in the meta-signature of acute rejection.

| Affymetrix Ids | Accession Number | Gene name | Gene symbol |
|---|---|---|---|
| 205758_at | NM_001768 NM_171827 | CD8 antigen, alpha | CD8A |
| 204912_at | NM_001558 | interleukin 10 receptor, alpha | IL10RA |
| 208885_at | NM_002298 | lymphocyte cytosolic protein 1 | L-plastin |
| 205269_at | NM_005565 | lymphocyte cytosolic protein 2 | SLP76 |
| 204891_s_at | NM_005356 | lymphocyte-specific protein tyrosine kinase | LCK |
| 204890_s_at | NM_005356 | lymphocyte-specific protein tyrosine kinase | LCK |
| 207957_s_at | X06318 | protein kinase C, beta 1 | PRKCB1 |
| 209685_s_at | NM_002738 | protein kinase C, beta 1, transcript variant 2 | PRKCB1 |
| 203761_at | NM_006748 | Src-like-adaptor | SLA |
| 203760_s_at | NM_006748 | Src-like-adaptor | SLA |
| 227817_at | BM684568 | similar to PKC beta 1 | PRKCB1 |
| 213603_s_at | NM_002872 | ras-related C3 botulinum toxin substrate 2 | Rac2 |
| 201288_at | NM_001175 | Rho GDP dissociation inhibitor beta | GDI |
| 209969_s_at | NM_139266 | signal transducer and activator of transcription 1 | STAT1 |

APC Infiltration and Activation (Monocytes/Macrophages)

Numerous signatures are associated with interstitial macrophages recruitment and functions such as phagocytosis, antigen presentation or reactive oxygen species production. Phagocytosis of macrophages is a key element in resolution of the injury. Macrophages and other APC have also a major role in T cell activation through antigen presentation via MHC molecules. The immunoproteasome machinery has an essential role in the regulation of the MHC system and is strongly activated by IFN-gamma. Macrophages and neutrophils are also specific producers of superoxide anion through the phagocyte NADPH oxidase pathway which might have a deleterious effect in the development of inflammation.

Phagosome/Lysosome Related Genes

| Affymetrix Ids | Accession Number | Gene name | Gene symbol |
|---|---|---|---|
| 201720_s_at | NM_006762 | Lysosomal-associated multispanning membrane protein-5 | LAPTM5 |

-continued

| Affymetrix Ids | Accession Number | Gene name | Gene symbol |
|---|---|---|---|
| 201721_s_at | NM_006762 | Lysosomal-associated multispanning membrane protein-5 | LAPTM5 |
| 1555745_a_at | NM_000239 | lysozyme | LYZ |
| 213975_s_at | NM_000239 | lysozyme (renal amyloidosis) | LYZ |
| 203471_s_at | NM_002664 | pleckstrin | PLEK |
| 203470_s_at | NM_002664 | pleckstrin | PLEK |

MHC and Related Genes

| Affymetrix Ids | Accession Number | Gene name | Gene symbol |
|---|---|---|---|
| 208729_x_at | NM_005514 | major histocompatibility complex, class I, B | HLA-B |
| 211799_x_at | NM_002117 | major histocompatibility complex, class I, C | HLA-C |
| 217478_s_at | NM_006120 | major histocompatibility complex, class II, DM alpha | HLA-DMA |
| 203932_at | NM_002118 | major histocompatibility complex, class II, DM beta | HLA-DMB |
| 211991_s_at | NM_033554 | major histocompatibility complex, class II, DP alpha 1 | HLA-DPA1 |
| 201137_s_at | NM_002121 | major histocompatibility complex, class II, DP beta 1 | HLA-DPB1 |
| 211656_x_at | NM_002123 | major histocompatibility complex, class II, DQ beta 1 | HLA-DQB1 |
| 212998_x_at | NM_002123 | major histocompatibility complex, class II, DQ beta 1 | HLA-DQB1 |
| 209823_x_at | NM_002123 | major histocompatibility complex, class II, DQ beta 1 | HLA-DQB1 |
| 211654_x_at | NM_002123 | major histocompatibility complex, class II, DQ beta 1 | HLA-DQB1 |
| 208894_at | NM_019111 | major histocompatibility complex, class II, DR alpha | HLA-DRA |
| 210982_s_at | NM_019111 | major histocompatibility complex, class II, DR alpha | HLA-DRA |
| 215193_x_at | NM_022555 NM_021983 | major histocompatibility complex, class II, DR beta | HLA-DRB |
| 209312_x_at | NM_002124 NM_002125 | major histocompatibility complex, class II, DR beta | HLA-DRB |

Immunoproteasome

| Affymetrix Ids | Accession Number | Gene name | Gene symbol |
|---|---|---|---|
| 202659_at | NM_002801 | proteasome (prosome, macropain) subunit, beta 10 | PSMB10 |
| 209040_s_at | NM_004159 NM_148919 | proteasome (prosome, macropain) subunit, beta 8 | PSMB8 |
| 204279_at | NM_002800 NM_148954 | proteasome (prosome, macropain) subunit, beta 9 | PSMB9 |
| 202307_s_at | NM_000593 | transporter 1, ATP-binding cassette, sub-family B | TAP1 |
| 205890_s_at | NM_006398 | ubiquitin D | UBD |

NADPH Oxidase Pathway Related Genes

| Affymetrix Ids | Accession Number | Gene name | Gene symbol |
|---|---|---|---|
| 203922_s_at | NM_000397 | cytochrome b-245, beta polypeptide | CYBB |
| 203471_s_at | NM_002664 | pleckstrin | PLEK |
| 203470_s_at | NM_002664 | pleckstrin | PLEK |
| 213603_s_at | NM_002872 | ras-related C3 botulinum toxin substrate 2 | Rac2 |

-continued

| Affymetrix Ids | Accession Number | Gene name | Gene symbol |
|---|---|---|---|
| 201288_at | NM_001175 | Rho GDP dissociation inhibitor beta | GDI |

IFN Gamma Pathway

All following genes are regulated (mainly induced) through INF-gamma and signal transduction through STAT1. These genes seem to be expressed preferentially in lymphocytes and macrophages. IFN-gamma effects include a massive impact on the inflammatory response observed in the rejected kidney and this pathway gathers the most up-regulated genes during AR.

| Affymetrix Ids | Accession Number | Gene name | Gene symbol |
|---|---|---|---|
| 1405_i_at | NM_002985 | chemokine (C-C motif) ligand 5 | CCL5 |
| 204655_at | NM_002985 | chemokine (C-C motif) ligand 5 | CCL5 |
| 204533_at | NM_001565 | chemokine (C—X—C motif) ligand 10 | CXCL10 |
| 203915_at | NM_002416 | chemokine (C—X—C motif) ligand 9 | CXCL9 |
| 205488_at | NM_006144 | granzyme A | GZMA |
| 202270_at | NM_002053 | guanylate binding protein 1, interferon-inducible, 67 kDa | GBP1 |
| 202269_x_at | NM_002053 | guanylate binding protein 1, interferon-inducible, 67 kDa | GBP1 |
| 231577_s_at | NM_002053 | guanylate binding protein 1, interferon-inducible, 67 kDa | GBP1 |
| 242907_at | AL832451 | similar to guanylate binding protein 2, interferon-inducible | GBP2 |
| 202659_at | NM_002801 | proteasome (prosome, macropain) subunit, beta 10 | PSMB10 |
| 209040_s_at | NM_004159 | proteasome (prosome, macropain) subunit, beta 8 | PSMB8 |

-continued

| Affymetrix Ids | Accession Number | Gene name | Gene symbol |
|---|---|---|---|
| 204279_at | NM_148919 NM_002800 NM_148954 | proteasome (prosome, macropain) subunit, beta 9 | PSMB9 |
| 202307_s_at | NM_000593 | transporter 1, ATP-binding cassette, sub-family B | TAP1 |
| 205890_s_at | NM_006398 | ubiquitin D | UBD |
| 209969_s_at | NM_139266 | signal transducer and activator of transcription 1 | STAT1 |
| 204698_at | NM_002201 | interferon stimulated gene 20 kDa | ISG20 |
| 33304_at | NM_002201 | interferon stimulated gene 20 kDa | ISG20 |

Apoptosis Related Genes

Most of the following genes are likely to be expressed by cytotoxic CD8 T cells and Th1 CD4 T cells. Caspase 1 is also considered to be an inflammatory marker because it regulates activation of IL-1.

| Affymetrix Ids | Accession Number | Gene name | Gene symbol |
|---|---|---|---|
| 209970_x_at | NM_001223 NM_033292 | caspase 1, apoptosis-related cysteine peptidase | CASP1 |
| 211366_x_at | NM_033293 | caspase 1, apoptosis-related cysteine peptidase | CASP1 |
| 211368_s_at | NM_033294 NM_033295 | caspase 1, apoptosis-related cysteine peptidase | CASP1 |
| 206011_at | BU675703 | similar to caspase 1, apoptosis-related cysteine protease | CASP1 |
| 206150_at | NM_001242 | tumor necrosis factor receptor superfamily, member 7 | CD27 |
| 205488_at | NM_006144 | granzyme A | GZMA |
| 201858_s_at | NM_002727 | proteoglycan 1, secretory granule | PRG1 |
| 205804_s_at | NM_025228 | TRAF3-interacting Jun N-terminal kinase | T3JAM |
| 213888_s_at | XM_514166 | TRAF3-interacting Jun N-terminal kinase (similar to) | T3JAM |

Integrin/Extracellular Matrix Related Genes

The following signatures are associated with the extracellular matrix and tissue remodeling (MMP7, TIMP1, tenascin C and versican) or directly with integrin signaling and cell motility.

| Affymetrix Ids | Accession Number | Gene name | Gene symbol |
|---|---|---|---|
| 202803_s_at | NM_000211 | integrin, beta 2 | ITGB2 |
| 1555349_a_at | NM_000211 | integrin, beta 2 | ITGB2 |
| 1557905_s_at | NM_001001389 NM_000610 | CD44 antigen, transcript variant 1 and 2, mRNA. | CD44 |
| 212063_at | NM_001001390 NM_001001391 | CD44 antigen, transcript variant 3 and 4, mRNA. | CD44 |
| 204220_at | NM_004877 | glia maturation factor, gamma | GMFG |
| 215646_s_at | NM_004385 | chondroitin sulfate proteoglycan 2 | CSPG2 |
| 213603_s_at | NM_002872 | ras-related C3 botulinum toxin substrate 2 | Rac2 |
| 201288_at | NM_001175 | Rho GDP dissociation inhibitor beta | GDI |
| 204197_s_at | NM_004350 | runt-related transcription factor 3 | RUNX3 |
| 204198_s_at | NM_004350 | runt-related transcription factor 3 | RUNX3 |
| 201645_at | NM_002160 | tenascin C | TNC |
| 237169_at | AL162425 | tenascin C | TNC |
| 204259_at | NM_002423 | matrix metalloproteinase 7 | MMP7 |
| 201666_at | NM_003254 | TIMP metallopeptidase inhibitor 1 | TIMP1 |

The data disclosed herein demonstrate that in actual clinical situations, and in the absence of molecular manipulations of gene expression, high levels of combination of genes are indicative of acute rejection. In one embodiment, the combination of up-regulated genes that form a molecular signature are those shown in Table 3.

It is anticipated that the analysis of more than one gene cluster will be useful not only for diagnosing transplant rejection but also for determining appropriate medical interventions. For example, acute rejection is a general description for a disorder that has many variations and many different optimal treatment strategies. In one embodiment, the invention provides a method for simultaneously identifying graft rejection and determining an appropriate treatment. In general, the invention provides methods comprising measuring representatives of different, informative gene clusters, that indicate an appropriate treatment protocol.

III. Detecting Gene Expression

In certain aspects the magnitude of expression is determined for one or more genes in sample obtained from a subject. The sample can comprise cells obtained from the subject, such as from a graft biopsy. Other samples include, but are not limited to fluid samples such as blood, plasma, serum, lymph, CSF, cystic fluid, ascites, urine, stool and bile. The sample may also be obtained from bronchoalveolar lavage fluid, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft.

In view of this specification, many different methods are known in the art for measuring gene expression. Classical methods include quantitative RT-PCR, Northern blots and ribonuclease protection assays. Certain examples described herein use competitive reverse transcription (RT)-PCR to measure the magnitude of expression of marker genes. Such methods may be used to examine expression of subject genes as well as entire gene clusters. However, as the number of genes to be examined increases, the time and expense may become cumbersome.

Large scale detection methods allow faster, less expensive analysis of the expression levels of many genes simultaneously. Such methods typically involve an ordered array of probes affixed to a solid substrate. Each probe is capable of hybridizing to a different set of nucleic acids. In one method, probes are generated by amplifying or synthesizing a substantial portion of the coding regions of various genes of interest. These genes are then spotted onto a solid support. mRNA samples are obtained, converted to cDNA, amplified and labeled (usually with a fluorescence label). The labeled cDNAs are then applied to the array, and cDNAs hybridize to their respective probes in a manner that is linearly related to their concentration. Detection of the label allows measurement of the amount of each cDNA adhered to the array.

Many methods for performing such DNA array experiments are well known in the art. Exemplary methods are described below but are not intended to be limiting.

Microarrays are known in the art and consist of a surface to which probes that correspond in sequence to gene products (e.g., cDNAs, mRNAs, oligonucleotides) are bound at known positions. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid derivative to which a particular cognate cDNA can specifically hybridize. The nucleic acid or derivative of the binding site can be, e.g., a synthetic oligomer, a full-length cDNA, a less-than full length cDNA, or a gene fragment.

Usually the microarray will have binding sites corresponding to at least 100 genes and more preferably, 500, 1000, 4000 or more. In certain embodiments, the most preferred arrays will have about 98-100% of the genes of a particular organism represented. In other embodiments, customized microarrays that have binding sites corresponding to fewer, specifically selected genes can be used. In certain embodiments customized microarrays comprise binding sites for fewer than 4000, fewer than 1000, fewer than 200 or fewer than 50 genes, and comprise binding sites for at least 2, preferably at least 3, 4, 5 or more genes of any of the clusters of Table 3. Preferably, the microarray has binding sites for genes relevant to testing and confirming a biological network model of interest.

The nucleic acids to be contacted with the microarray may be prepared in a variety of ways. Methods for preparing total and poly(A)+ RNA are well known and are described generally in Sambrook et al., supra. Labeled cDNA is prepared from mRNA by oligo dT-primed or random-primed reverse transcription, both of which are well known in the art (see e.g., Klug and Berger, 1987, Methods Enzymol. 152:316&325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Nature Biotech. 14:1675). The cDNAs or RNAs can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescent labels are used, many suitable fluorophores are known, including fluorescein, lissamine, phycoerythrin, rhodamine (Perkin Elmer Cetus), Cy2, Cy3, Cy3.5, Cy5, Cy5.5, Cy7, Fluor X (Amersham) and others (see, e.g., Kricka, 1992, Academic Press San Diego, Calif.).

In another embodiment, a label other than a fluorescent label is used. For example, a radioactive label, or a pair of radioactive labels with distinct emission spectra, can be used (see Zhao et al., 1995, Gene 156:207; Pietu et al., 1996, Genome Res. 6:492). However, use of radioisotopes is a less-preferred embodiment.

Nucleic acid hybridization and wash conditions are chosen so that the population of labeled nucleic acids will specifically hybridize to appropriate, complementary nucleic acids affixed to the matrix. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch Optimal hybridization conditions will depend on the length (e.g., oligomer versus polynucleotide greater than 200 bases) and type (e.g., RNA, DNA, PNA) of labeled nucleic acids and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array can be, preferably, detected by scanning confocal laser microscopy. When two fluorophores are used, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Research 6:639-645). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6:639-645 and in other references cited herein. Alternatively, the fiber-optic bundle described by Ferguson et al., 1996, Nature Biotech. 14:1681-1684, may be used to monitor mRNA abundance levels at a large number of sites simultaneously. Fluorescent microarray scanners are commercially available from Affymetrix, Packard BioChip Technologies, BioRobotics and many other suppliers.

Signals are recorded, quantitated and analyzed using a variety of computer software. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores is preferably calculated. The ratio is independent of the absolute expression level of the cognate gene, but is useful for genes whose expression is significantly modulated by drug administration, gene deletion, or any other tested event.

In one embodiment, transcript arrays reflecting the transcriptional state of a cell of interest are made by hybridizing a mixture of two differently labeled sets of cDNAs to the microarray. One cell is a cell of interest while the other is used as a standardizing control. The relative hybridization of each cell's cDNA to the microarray then reflects the relative expression of each gene in the two cells.

In preferred embodiments, expression levels in different samples and conditions may be compared using a variety of statistical methods. A variety of statistical methods are available to assess the degree of relatedness in expression patterns of different genes. The statistical methods may be broken into two related portions: metrics for determining the relatedness of the expression pattern of one or more gene, and clustering methods, for organizing and classifying expression data based on a suitable metric (Sherlock 2000, Curr. Opin. Immunol. 12:201-205; Butte et al., 2000, Pacific Symposium on Biocomputing, Hawaii, World Scientific, p. 418-29).

In one embodiment, Pearson correlation may be used as a metric. In brief, for a given gene, each data point of gene expression level defines a vector describing the deviation of the gene expression from the overall mean of gene expression level for that gene across all conditions. Each gene's expression pattern can then be viewed as a series of positive and negative vectors. A Pearson correlation coefficient can then be calculated by comparing the vectors of each gene to each other. An example of such a method is described in Eisen et al. (1998, supra). Pearson correlation coefficients account for the direction of the vectors, but not the magnitudes.

In another embodiment, Euclidean distance measurements may be used as a metric. In these methods, vectors are calculated for each gene in each condition and compared on the basis of the absolute distance in multidimensional space between the points described by the vectors for the gene. In another embodiment, both Euclidean distance and Correlation coefficient were used in the clustering.

In a further embodiment, the relatedness of gene expression patterns may be determined by entropic calculations (Butte et al. 2000, supra). Entropy is calculated for each gene's expression pattern. The calculated entropy for two genes is then compared to determine the mutual information. Mutual information is calculated by subtracting the entropy of the joint gene expression patterns from the entropy for calculated for each gene subjectly. The more different two gene expression patterns are, the higher the joint entropy will be and the lower the calculated mutual information. Therefore, high mutual information indicates a non-random relatedness between the two expression patterns.

In another embodiment, agglomerative clustering methods may be used to identify gene clusters. In one embodiment, Pearson correlation coefficients or Euclidean metrics are determined for each gene and then used as a basis for forming a dendrogram. In one example, genes were scanned for pairs of genes with the closest correlation coefficient. These genes are then placed on two branches of a dendrogram connected by a node, with the distance between the depth of the branches proportional to the degree of correlation. This process continues, progressively adding branches to the tree. Ultimately a tree is formed in which genes connected by short branches represent clusters, while genes connected by longer branches represent genes that are not clustered together. The points in multidimensional space by Euclidean metrics may also be used to generate dendrograms.

In yet another embodiment, divisive clustering methods may be used. For example, vectors are assigned to each gene's expression pattern, and two random vectors are generated. Each gene is then assigned to one of the two random vectors on the basis of probability of matching that vector. The random vectors are iteratively recalculated to generate two centroids that split the genes into two groups. This split forms the major branch at the bottom of a dendrogram. Each group is then further split in the same manner, ultimately yielding a fully branched dendrogram.

In a further embodiment, self-organizing maps (SOM) may be used to generate clusters. In general, the gene expression patterns are plotted in n-dimensional space, using a metric such as the Euclidean metrics described above. A grid of centroids is then placed onto the n-dimensional space and the centroids are allowed to migrate towards clusters of points, representing clusters of gene expression. Finally the centroids represent a gene expression pattern that is a sort of average of a gene cluster. In certain embodiments, SOM may be used to generate centroids, and the genes clustered at each centroid may be further represented by a dendrogram. An exemplary method is described in Tamayo et al., 1999, PNAS 96:2907-12. Once centroids are formed, correlation must be evaluated by one of the methods described supra.

In another aspect, the invention provides probe sets. Preferred probe sets are designed to detect expression of one or more genes and provide information about the status of a graft. Preferred probe sets of the invention comprise probes that are useful for the detection of at least two genes belonging to any of the gene clusters of Table 1. Particularly preferred probe sets will comprise probes useful for the detection of at least one, two, three, four or at least five genes belonging to any of the gene clusters of Table 3. Probe sets of the invention comprise probes useful for the detection of no more than 10,000 gene transcripts, and preferred probe sets will comprise probes useful for the detection of fewer than 4000, fewer than 1000, fewer than 200, fewer than 100, fewer than 90, fewer than 80, fewer than 70, fewer than 60, fewer than 50, fewer than 40, fewer than 30, fewer than 20, fewer than 10 gene transcripts. The probe sets of the invention are targeted at the detection of gene transcripts that are informative about transplant status. Probe sets of the invention may also comprise a large or small number of probes that detect gene transcripts that are not informative about transplant status. In preferred embodiments, probe sets of the invention are affixed to a solid substrate to form an array of probes. It is anticipated that probe sets may also be useful for multiplex PCR. The probes of probe sets may be nucleic acids (eg. DNA, RNA, chemically modified forms of DNA and RNA), or PNA, or any other polymeric compound capable of specifically interacting with the desired nucleic acid sequences.

Computer readable media comprising a marker(s) of the present invention is also provided. As used herein, "computer readable media" includes a medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a marker of the present invention.

As used herein, "recorded" includes a process for storing information on computer readable medium. Those skilled in the art can readily adopt any of the presently known methods for recording information on computer readable medium to generate manufactures comprising the markers of the present invention.

A variety of data processor programs and formats can be used to store the marker information of the present invention on computer readable medium. For example, the nucleic acid sequence corresponding to the markers can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g. text file or database) may be adapted in order to obtain computer readable medium having recorded thereon the markers of the present invention.

By providing the markers of the invention in computer readable form, one can routinely access the marker sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

The invention also includes an array comprising a marker(s) of the present invention. The array can be used to assay expression of one or more genes in the array. In one embodiment, the array can be used to assay gene expression in a tissue to ascertain tissue specificity of genes in the array. In this manner, up to about 8600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development and differentiation, disease progression, in vitro processes, such a cellular transformation and senescence, autonomic neural and neurological processes, such as, for example, pain and appetite, and cognitive functions, such as learning or memory.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and diseased cells. This provides a battery of genes that could serve as a molecular target for diagnosis or therapeutic intervention.

IV. Proteins

It is further anticipated that increased levels of certain proteins may also provide diagnostic information about transplants. In certain embodiments, one or more proteins encoded by genes of any of the gene clusters of Table 3 may be detected, and elevated or decreased protein levels may be used to diagnose graft rejection. In a preferred embodiment, protein levels are detected in a post-transplant fluid sample, and in a particularly preferred embodiment, the fluid sample is peripheral blood or urine. In another preferred embodiment, protein levels are detected in a graft biopsy.

In view of this specification, methods for detecting proteins are well known in the art. Examples of such methods include Western blotting, enzyme-linked immunosorbent assays (ELISAs), one- and two-dimensional electrophoresis, mass spectroscopy and detection of enzymatic activity. Suitable antibodies may include polyclonal, monoclonal, fragments (such as Fab fragments), single chain antibodies and other forms of specific binding molecules.

V. Predictive Medicine

The present invention pertains to the field of predictive medicine in which diagnostic assays, prognostic assays, pharmacogenetics and monitoring clinical trials are used for prognostic (predictive) purposes to thereby diagnose and treat an subject prophylactically. Accordingly, one aspect of the present invention relates to diagnostic assays for determining marker protein and/or nucleic acid expression from a sample (e.g., blood, serum, cells, tissue) to thereby determine whether a subject is likely to reject a transplant.

Another aspect of the invention pertains to monitoring the influence of agents (e.g., drugs, compounds) on the expression or activity of marker in clinical trials as described in further detail in the following sections.

An exemplary method for detecting the presence or absence of marker protein or genes of the invention in a sample involves obtaining a sample from a test subject and contacting the sample with a compound or an agent capable of detecting the protein or nucleic acid (e.g., mRNA, genomic DNA) that encodes the marker protein such that the presence of the marker protein or nucleic acid is detected in the sample. A preferred agent for detecting mRNA or genomic DNA corresponding to a marker gene or protein of the invention is a labeled nucleic acid probe capable of hybridizing to a mRNA or genomic DNA of the invention. Suitable probes for use in the diagnostic assays of the invention are described herein.

A preferred agent for detecting marker protein is an antibody capable of binding to marker protein, preferably an antibody with a detectable label. Antibodies can be polyclonal, or more preferably, monoclonal. An intact antibody, or a fragment thereof (eg., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "sample" is intended to include tissues, cells and biological fluids isolated from a subject, as well as tissues, cells and fluids present within a subject. That is, the detection method of the invention can be used to detect marker mRNA, protein, or genomic DNA in a sample in vitro as well as in vivo. For example, in vitro techniques for detection of marker mRNA include Northern hybridizations and in situ hybridizations. In vitro techniques for detection of marker protein include enzyme linked immunosorbent assays (ELISAs), Western blots, immunoprecipitations and immunofluorescence. In vitro techniques for detection of marker genomic DNA include Southern hybridizations. Furthermore, in vivo techniques for detection of marker protein include introducing into a subject a labeled anti-marker antibody. For example, the antibody can be labeled with a radioactive marker whose presence and location in a subject can be detected by standard imaging techniques.

In one embodiment, the sample contains protein molecules from the test subject. Alternatively, the sample can contain mRNA molecules from the test subject or genomic DNA molecules from the test subject. A preferred sample is a serum sample isolated by conventional means from a subject.

The methods further involve obtaining a control sample (e.g., biopsies from non transplanted healthy kidney or from transplanted healthy kidney showing no sign of rejection) from a control subject, contacting the control sample with a compound or agent capable of detecting marker protein, mRNA, or genomic DNA, such that the presence of marker protein, mRNA or genomic DNA is detected in the sample, and comparing the presence of marker protein, mRNA or genomic DNA in the control sample with the presence of marker protein, mRNA or genomic DNA in the test sample.

The invention also encompasses kits for detecting the presence of marker in a sample. For example, the kit can comprise a labeled compound or agent capable of detecting marker protein or mRNA in a sample; means for determining the amount of marker in the sample; and means for comparing the amount of marker in the sample with a standard. The compound or agent can be packaged in a suitable container. The kit can further comprise instructions for using the kit to detect marker protein or nucleic acid.

The diagnostic methods described herein can furthermore be utilized to identify subjects having or at risk of developing a disease or disorder associated with aberrant marker expression or activity. As used herein, the term "aberrant" includes a marker expression or activity which deviates from the wild type marker expression or activity. Aberrant expression or activity includes increased or decreased expression or activity, as well as expression or activity which does not follow the wild type developmental pattern of expression or the subcellular pattern of expression. For example, aberrant marker expression or activity is intended to include the cases in which a mutation in the marker gene causes the marker gene to be under-expressed or over-expressed and situations in which such mutations result in a nonfunctional marker protein or a protein which does not function in a wild-type fashion, e.g., a protein which does not interact with a marker ligand or one which interacts with a non-marker protein ligand.

Furthermore, the prognostic assays described herein can be used to determine whether a subject can be administered an agent (e.g., an agonist, antagonist, peptidomimetic, protein, peptide, nucleic acid, small molecule, or other drug candidate) to reduce the risk of rejection, e.g., cyclospsorin. Thus, the present invention provides methods for determining whether a subject can be effectively treated with an agent for a disorder associated with increased gene expression or activity of the combination of genes in Table 3

Monitoring the influence of agents (e.g., drugs) on the expression or activity of a genes can be applied not only in basic drug screening, but also in clinical trials. For example, the effectiveness of an agent determined by a screening assay as described herein to increase gene expression, protein levels, or upregulate activity, can be monitored in clinical trials of subjects exhibiting by examining the molecular signature and any changes in the molecular signature during treatment with an agent.

For example, and not by way of limitation, genes and their encoded proteins that are modulated in cells by treatment with an agent (e.g., compound, drug or small molecule) which modulates gene activity can be identified. In a clinical trial, cells can be isolated and RNA prepared and analyzed for the levels of expression of genes implicated associated with rejection. The levels of gene expression (e.g., a gene expression pattern) can be quantified by northern blot analysis or RT-PCR, as described herein, or alternatively by measuring the amount of protein produced, by one of the methods as described herein. In this way, the gene expression pattern can serve as a molecular signature, indicative of the physiological response of the cells to the agent. Accordingly, this response state may be determined before, and at various points during treatment of the subject with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a gene or combination of genes, the protein encoded by the genes, mRNA, or genomic DNA in the preadministration sample; (iii) obtaining one or more post-administration samples from the subject; (iv) detecting the level of expression or activity of the marker protein, mRNA, or genomic DNA in the post-administration samples; (v) comparing the level of expression or activity of the marker protein, mRNA, or genomic DNA in the pre-administration sample with the a gene or combination of genes, the protein encoded by the genes, mRNA, or genomic DNA in the post administration sample or samples; and (vi) altering the administration of the agent to the subject accordingly. For example, increased administration of the agent may be desirable to decrease the expression or activity of the genes to lower levels, i.e., to increase the effectiveness of the agent to protect against transplant rejection. Alternatively, decreased administration of the agent may be desirable to decrease expression or activity of marker to lower levels than detected, i.e. to decrease the effectiveness of the agent e.g., to avoid toxicity. According to such an embodiment, gene expression or activity may be used as an indicator of the effectiveness of an agent, even in the absence of an observable phenotypic response.

The present invention provides for both prophylactic and therapeutic methods for preventing transplant rejection. With regards to both prophylactic and therapeutic methods of treatment, such treatments may be specifically tailored or modified, based on knowledge obtained from the field of pharmacogenomics. "Pharmacogenomics", as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype", or "drug response genotype".) Thus, another aspect of the invention provides methods for tailoring an subject's prophylactic or therapeutic treatment with either the marker molecules of the present invention or marker modulators according to that subject's drug response genotype. Pharmacogenomics allows a clinician or physician to target prophylactic or therapeutic treatments to subjects who will most benefit from the treatment and to avoid treatment of subjects who will experience toxic drug related side effects.

In one aspect, the invention provides a method for preventing transplant rejection in a subject, associated with increased marker expression or activity, by administering to the subject a compound or agent which modulates marker expression. Examples of such compounds or agents are e.g. compounds or agents having immunosuppressive properties, e.g. as used in transplantation, e.g. a calcineurin inhibitor, e.g. cyclosporin A or FK 506; a mTOR inhibitor, e.g. rapamycin, 40-O-(2-hydroxyethyl)-rapamycin, CC1779, ABT578, AP23573, biolimus-7 or biolimus-9; an ascomycin having immunosuppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidenecyanoacetamide a-cyano-(3,4-dihydroxy)-]N-benzylcinnamamide (Tyrphostin AG 490), prodigiosin 25-C (PNU 156804), [4-(4'-hydroxyphenyl)-amino-6,7-dimethoxyquinazoline] (WHI-P131), [4-(3'-bromo-4'-hydroxyphenyl)-amino-6,7-dimethoxyquinazoline] (WHI-P154), [4-(3', 5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a SIP receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists. These compounds or agents may also be used in combination.

Another aspect of the invention pertains to methods of modulating marker protein expression or activity for therapeutic purposes. Accordingly, in an exemplary embodiment, the modulatory method of the invention involves contacting a cell with a marker protein or agent that modulates one or more of the activities of a marker protein activity associated with the cell. An agent that modulates marker protein activity can be an agent as described herein, such as a nucleic acid or a protein, a naturally-occurring target molecule of a marker protein (e.g., a marker protein substrate), a marker protein antibody, a marker protein agonist or antagonist, a peptidomimetic of a marker protein agonist or antagonist, or other small molecule. In one embodiment, the agent stimulates one or more marker protein activities. Examples of such stimulatory agents include active marker protein and a nucleic acid molecule encoding marker protein that has been introduced into the cell. In another embodiment, the agent inhibits one or more marker protein activities. Examples of such inhibitory agents include antisense marker protein nucleic acid molecules, anti-marker protein antibodies, and marker protein inhibitors. These modulatory methods can be performed in vitro (e.g., by culturing the cell with the agent) or, alternatively, in vivo (e.g., by administering the agent to a subject). As such, the present invention provides methods of treating an subject afflicted with a disease or disorder characterized by aberrant expression or activity of a marker protein or nucleic acid molecule. In one embodiment, the method involves administering an agent (e.g., an agent identified by a screening assay described herein), or combination of agents that modulates (e.g., upregulates or downregulates) marker protein expression or activity. In another embodiment, the method involves administering a marker protein or nucleic acid molecule as therapy to compensate for reduced or aberrant marker protein expression or activity.

Stimulation of marker protein activity is desirable in situations in which marker protein is abnormally downregulated and/or in which increased marker protein activity is likely to have a beneficial effect. For example, stimulation of marker protein activity is desirable in situations in which a marker is downregulated and/or in which increased marker protein activity is likely to have a beneficial effect. Likewise, inhibition of marker protein activity is desirable in situations in which marker protein is abnormally up-regulated and/or in which decreased marker protein activity is likely to have a beneficial effect.

The marker protein and nucleic acid molecules of the present invention, as well as agents, or modulators which have a stimulatory or inhibitory effect on marker protein activity (e.g., marker gene expression) as identified by a screening assay described herein can be administered to subjects to treat (prophylactically or therapeutically) marker-associated disorders (e.g., prostate cancer) associated with aberrant marker protein activity. In conjunction with such treatment pharmacogenomics (i.e., the study of the relationship between an subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a marker molecule or marker modulator as well as tailoring the dosage and/or therapeutic regimen of treatment with a marker molecule or marker modulator.

One pharmacogenomics approach to identifying genes that predict drug response, known as "a genome-wide association", relies primarily on a high-resolution map of the human genome consisting of already known gene-related markers (e.g. a "bi-allelic" gene marker map which consists of 60,000-100,000 polymorphic or variable sites on the human genome, each of which has two variants.) Such a high-resolution genetic map can be compared to a map of the genome of each of a statistically significant number of subjects taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, subjects can be grouped into genetic categories depending on a particular pattern of SNPs in their subject genome. In such a manner, treatment regimens can be tailored to groups of genetically similar subjects, taking into account traits that may be common among such genetically similar subjects.

Alternatively, a method termed the "candidate gene approach", can be utilized to identify genes that predict drug response. According to this method, if a gene that encodes a drugs target is known (e.g., a marker protein of the present invention), all common variants of that gene can be fairly easily identified in the population and it can be determined if having one version of the gene versus another is associated wit h a particular drug response.

Information generated from more than one of the above pharmacogenomics approaches can be used to determine appropriate dosage and treatment regimens for prophylactic or therapeutic treatment an subject. This knowledge, when applied to dosing or drug selection, can avoid adverse reactions or therapeutic failure and thus enhance therapeutic or prophylactic efficiency when treating a subject with a marker molecule or marker modulator, such as a modulator identified by one of the exemplary screening assays described herein.

This invention is further illustrated by the following examples which should not be construed as limiting. The contents of all references, patents and published patent applications cited throughout this application, are incorporated herein by reference.

EXAMPLES

Example 1

Identifying a Gene Expression Signature Indicative of Acute Rejection 2.1 Data Collection Two microarray datasets were downloaded from Gene Expression Omnibus (GEO). One analysis performed on a customized two-channel cDNA microarray platform (Lymphochip) through accession number GDS365 (Dataset D) (Stanford et al. New England Journal of Medicine 2003; 349(2):125-138). This study, published in 2003, is considered as a reference in gene expression profiling of kidney transplants. Another analysis, performed on the Affymetrics U95A version 2 platform is available through the accession number GDS724 (Dataset A) (Flechner et al. American Journal of Transplantation 2004; 4(9): 1475-1489). These two public datasets were compared with three internal analyses, including dataset C and the dataset B, both performed on Affymetrix HG-U133 Plus2 chips. In addition to these human studies, the meta-analysis study was performed on a non human primate (NHP) (dataset E), (Novartis RDS no: RD-2003-02871) using Affymetrix HG-U133A. Finally the meta-analysis includes a total number of 40 acute (AR) plus borderline, 61 normal non-rejected (normal) and 22 non-transplanted control kidney biopsies (control) (Table 1). All data in meta-analyses were generated in the Affymetrix platform except the dataset D which was based on a two-channel cDNA microarray.

TABLE 1

| Dataset | Number of samples per dataset | | | |
|---|---|---|---|---|
| | control | normal | borderline | acute |
| A | 9 | 10 | | 7 |
| B | | 30 | 8 | 4 |
| C | 13 | | 7 | 8 |
| D | | 15 | | 15 |
| Total human samples E | 22 | 55 6 | 15 | 34 6 |
| Global Total | 22 | 61 | 15 | 40 |

2.2 Initial Data Analysis 2.2.1 Statistical Filtering

For all datasets, the same pair-wise comparison between normal or control versus borderline and acute rejection samples was performed For the studies performed in Affymetrix microarrays, MAS5 normalized gene expression values were subjected to the following analysis procedure:

raw value $>=80$ in 75% of chips of the minimum group.

one way ANOVA ($p<=0.05$)

fold change $>=2$

Because dataset D was based on a two-channel cDNA microarray, a unlog2 ratio value was used and applied one way ANOVA ($p<=0.05$) and fold change 2 between tested conditions.

The resulting probesets from different analysis were translated to HG_U 133_plus2 chip identifiers (see mapping) and intersected to identify common gene expression signatures.

2.2.2 Mapping

Two different strategies were used to map results from different platforms (HG_U95Av2, HG-U133A, cDNA microarray) to the HG-U133_Plus-2 platform.

1) Strategy for results from Affymetrix HG U95Av2 and HG-U133A chips.

Direct mapping probesets from HG_U95Av2 or HG-U133A to HG-U133_Plus-2 was done through the "Sequence Set Mapping" functionality of Demon application at Novartis.

2) Strategy for results from cDNA microarray Lymphochip (datasetD).

The results from the dataset D analysis include cDNA fragments with NCBI accession number. Sequences of these fragment were downloaded through SRS, an in-house database at Novartis. BLAST application was further applied to map cDNA fragments to Human Refseq transcripts and Compugen Human Transcripts by defining a hit, whose alignment contains $>=75$% length of input cDNA fragment sequence and shares $>=95$% identity in the alignment. The outputs from RefReq and Compugen were analyzed by Demon to map these transcript hits to the probesets in HG-U133_Plus-2 chip.

2.2.3 Independent Dataset Analysis

Dataset A

MAS5 raw values were imported from GEO and analyzed in Gene Spring using the HG-U95Av2 genome. This dataset is comprised of kidney biopsies obtained from 9 living donor controls, 7 recipients with histologically confirmed acute rejection, and 10 protocol biopsies carried out more than one year post transplant in patients with good transplant function an normal histology. Using the statistical filtering previously described, 470 probesets were selected for the comparison between acute and healthy non-transplanted (normal) kidney (FIG. 1). The comparison between acute and normal samples returns 871 probesets. These two genelists were then translated from HG_U95Av2 to HG_U133_plus 2 (see mapping) and returns 1420 probesets that will be further used for the meta-analysis.

Remark: A lot of genes are changing both in AR and normal compared to control. Normal samples show no clinical evidence of rejection but indicate a sub-activation status in term of gene expression reflecting a future or already passed acute episode. This subacute activation likely anticipate a future rejection response.

Dataset B

MAS5 raw values were downloaded from NPGN (in-house database at Novartis) and analyses into Genespring using the HG-U133A_plus2 genome. This dataset is comprised of 3 serial diagnostic biopsies per patient for a total of 30 patients. Kinetics of the visits post transplantation were 6, 12 and 24 weeks. This study was elaborated in collaboration between Novartis and Prof. Hannover from Medizinische Hochschule of Hannover, Germany. Only the healthy biopsies from patients that will not show a sign of rejection during the course of the study were used. This represents 30 healthy different biopsies. Using the statistical filtering previously described, 969 probesets were selected for the comparison between acute and healthy transplanted kidney (normal). The comparison between acute and borderline returns 140 probesets. The union list returns 1088 probesets (FIG. 1).

Dataset C

Raw data were downloaded from GDL and analyzed in Genespring using the HG-U133A_plus2 genome. This dataset is comprised of 13 samples of normal kidneys from control, nephrectomized patients; 7 borderline biopsies, 9 renal biopsies with acute rejection (AR) and 7 renal biopsies with acute rejection on top of CAN (AR+CR). Renal core biopsies were sampled in RNAlater (Ambion) and RNA was extracted by RNeasy (Qiagen). 50 ng of high-quality total RNA was subjected to Affymetrix 2-cycle cDNA synthesis amplification (Affy SSTv2), fluorescent labeling and hybridization to the HG-U133 Plus 2 human genome array. 13 additional biopsies from normal transplanted kidney were available but not included in the meta-analysis because of high heterogeneity in this group. Using the statistical filtering previously described, 1611 probesets were selected for the comparison between acute and healthy non-transplanted kidney. The comparison between acute and borderline returns 420 probesets and the comparison between healthy and borderline returns 851 probesets. The union list returns 2182 probesets (FIG. 1).

Dataset D

In this analysis, a total of 59 samples were from pediatric renal-allograft recipients (between 1 month and 10 years after transplantation during acute allograft dysfunction, defined by an increase of more than 10 percent in the serum Creatinine concentration from base line), and 8 were from donors. All biopsy samples were snap frozen. The microarray experiment is performed on a Lymphochip, which contains 28,032 DNA spots representing approximately 12,440 human genes. Total RNA was isolated from frozen biopsy samples (TRI Reagent, Molecular Research Center). A common reference pool of RNA was used as an internal standard. Sample or reference RNA was subjected to two successive rounds of amplification before undergoing hybridization to microarrays. Log 2 ratio values were downloaded from GEO, transformed into linear value and re-analyzed into Genespring with the previously defined statistical filtering. To keep consistency of analyses among different datasets, normal samples (15 biopsies) versus acute type I and II (total of 15 acute biopsies) were compared but type III samples were discarded These types refer to different level of AR used in this analysis to classify the biopsies. In our global analysis we considered Type I and II as similar and never included type III because this level of rejection is extremely rare. This new analysis returns 842 probesets in the lymphochips analysis and 790 after mapped to the HG-U133_plus2 chips (see mapping).

Dataset E-Non Human Primate

Mas5 raw data were exported from NPGN database and analyzed in Genespring using the HG_U133A genome. This study was performed with cynomolgus kidney allografts collected, at various times after transplantation. Biopsies were histologically diagnosed as acute rejection, borderline and normal. For each graft the cortex was dissected and snap-frozen in liquid nitrogen. The normal versus AR comparison (n=6 in each group) returns 2636 genes significantly changing more than 2 folds and 4430 probesets after translation in the HG-U133 Plus 2 chip (FIG. 1).

3 RESULTS

3.1 Meta-Signature of Kidney Acute Rejection

To identify systematic gene expression signatures for acute rejection, we intersected the resulting genelists of each dataset. Table 2 show the successive overlaps between the 4 human and the NHP datasets.

TABLE 2

Intersections of acute rejection signatures among the 5 re-analysed dataset.

| Dataset | D | B | C | A | E |
|---|---|---|---|---|---|
| D | 790 | 188 | 236 | 289 | 341 |
| D/B | | | 152 | 110 | 126 |
| D/B/C | | | | 95 | 106 |
| D/B/C/A | | | | | |

Figure 2:
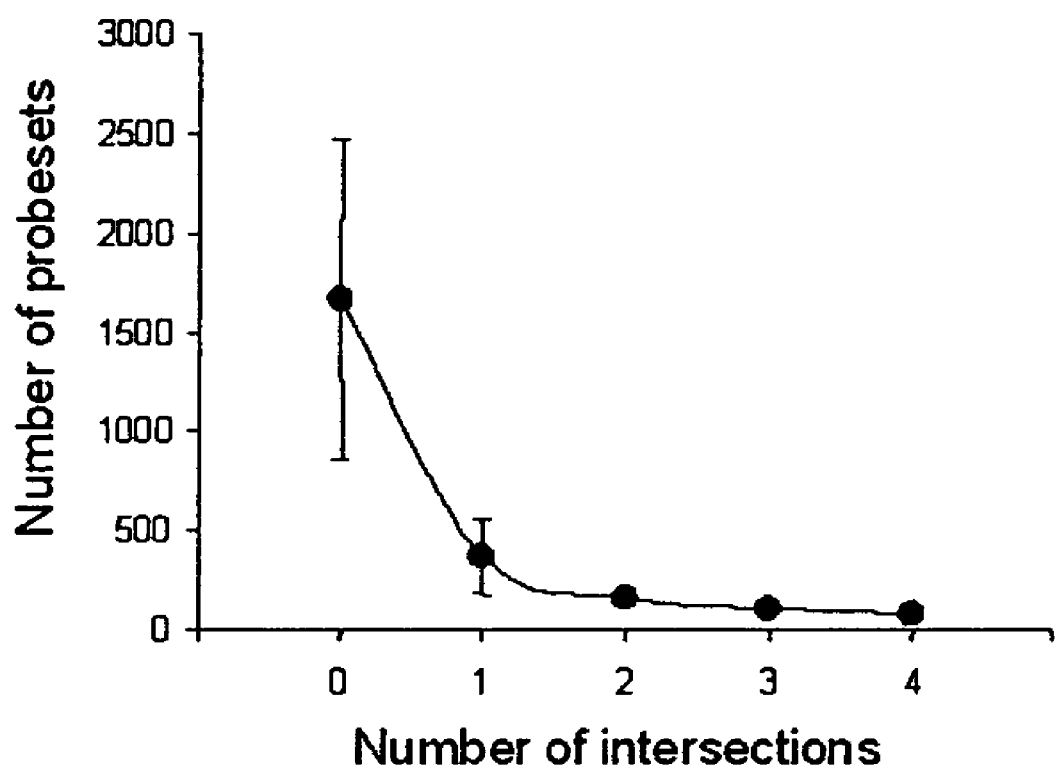
FIG. 2 is a graph showing the overlapping results of various datasets.

This strategy reveals a common transcriptional profile of 57 genes represented by 81 Affymetrix probesets that are systematically up-regulated in all the acute samples compared to normal or healthy kidneys (Table 3). It is interesting to see that 95 probesets are systematically found in the 4 human datasets. Among those, 81 are confirmed through the NHP analysis (Table 2). FIG. 2 shows the number of probeset-intersections evolution according to the number of dataset overlapped. Intersection of 2 datasets (independently of their order of intersection) induced a severe drop in the overlapped genes. This phenomenon is certainly explained by the high variability in the data analyzed. However increasing the number of overlap does not induce a strong diminution of the number of genes and the intersection curve tends to plateau. This result suggests that this method of intersection is able to identify a set of genes that are consistently found as robust signatures for acute allograft rejection (Table 3).

Importantly, these 57 genes are mainly hematopoietic cell specific and reflect T cells, B cells and Antigen Presenting Cells (APC, monocytes/dendritic cells/macrophages) infiltration in the transplanted organ. Immunoproteasome and major histocompatibility class I and II pathways as well as IFN-γ, chemokine, apoptosis and integrin signaling represent the other predominant biological functions associated with this transcriptional profile. Therefore, this meta-analysis extracts the most important and consistent features known to be important in the pathophysiology of acute rejection (Halloran et al. N Engl J Med 2004; 351(26):2715-2729), and provides a good basis for further biomarkers discovery. Surprisingly, the human phagocyte NADPH oxidase pathway appears to be highly conserved among all the datasets, suggesting that production of superoxide anion by activated macrophages and neutrophils might play an important role in the acute rejection process leading to kidney injury.

TABLE 3 acute meta-signature.

| Affymetrix Ids | Accession Number | Gene name | Gene symbol |
| --- | --- | --- | --- |
| 209970_x_at | NM_001223 NM_033292 | caspase 1, apoptosis-related cysteine peptidase | CASP1 |
| 211366_x_at | NM_033293 | caspase 1, apoptosis-related cysteine peptidase | CASP1 |
| 211368_s_at | NM_033294 NM_033295 | caspase 1, apoptosis-related cysteine peptidase | CASP1 |
| 206011_at | BU675703 | similar to caspase 1, apoptosis-related cysteine protease | CASP1 |
| 1557905_s_at | NM_001001389 NM_000610 | CD44 antigen, transcript variant 1 and 2, mRNA. | CD44 |
| 212063_at | NM_001001390 NM_001001391 | CD44 antigen, transcript variant 3 and 4, mRNA. | CD44 |
| 204118_at | NM_001778 | CD48 antigen | CD48 |
| 204661_at | NM_001803 | CD52 antigen | CD52 |
| 34210_at | NM_001803 | CD52 antigen | CD52 |
| 203416_at | NM_000560 | CD53 antigen | CD53 |
| 242946_at | AL391064 | CD53 antigen | CD53 |
| 205758_at | NM_001768 NM_171827 | CD8 antigen, alpha | CD8A |
| 227817_at | BM684568 | cDNA clone IMAGE: 38786 3 | |
| 1405_i_at | NM_002985 | chemokine (C-C motif) ligand 5 | CCL5 |
| 204655_at | NM_002985 | chemokine (C-C motif) ligand 5 | CCL5 |
| 204533_at | NM_001565 | chemokine (C—X—C motif) ligand 10 | CXCL10 |
| 203915_at | NM_002416 | chemokine (C—X—C motif) ligand 9 | CXCL9 |
| 215646_s_at | NM_004385 | chondroitin sulfate proteoglycan 2 | CSPG2 |
| 203922_s_at | NM_000397 | cytochrome b-245, beta polypeptide | CYBB |
| 204220_at | NM_004877 | glia maturation factor, gamma | GMFG |
| 205488_at | NM_006144 | granzyme A | GZMA |
| 202270_at | NM_002053 | guanylate binding protein 1, interferon-inducible, 67 kDa | GBP1 |
| 202269_x_at | NM_002053 | guanylate binding protein 1, interferon-inducible, 67 kDa | GBP1 |
| 231577_s_at | NM_002053 | guanylate binding protein 1, interferon-inducible, 67 kDa | GBP1 |
| 242907_at | AL832451 | similar to guanylate binding protein 2, interferon-inducible | GBP2 |
| 202957_at | NM_005335 | hematopoietic cell-specific Lyn substrate 1 | HCLS1 |
| 208018_s_at | NM_002110 | hemopoietic cell kinase | HCK |
| 212827_at | BC089412 | similar to IgM heavy chain | IGHM |
| 217022_s_at | S55735 | immunoglobulin alpha1 heavy chain (similar to) | IGHA1 |
| 209374_s_at | XM_522973 | immunoglobulin heavy constant mu (similar to) | IGHM |
| 202803_s_at | NM_000211 | integrin, beta 2 | ITGB2 |
| 1555349_a_at | NM_000211 | integrin, beta 2 | ITGB2 |
| 204698_at | NM_002201 | interferon stimulated gene 20 kDa | ISG20 |
| 33304_at | NM_002201 | interferon stimulated gene 20 kDa | ISG20 |
| 204912_at | NM_001558 | interleukin 10 receptor, alpha | IL10RA |
| 208885_at | NM_002298 | lymphocyte cytosolic protein 1 | L-plastin |
| 205269_at | NM_005565 | lymphocyte cytosolic protein 2 | SLP76 |
| 204891_s_at | NM_005356 | lymphocyte-specific protein tyrosine kinase | LCK |
| 204890_s_at | NM_005356 | lymphocyte-specific protein tyrosine kinase | LCK |
| 201720_s_at | NM_006762 | Lysosomal-associated multispanning membrane protein-5 | LAPTM5 |
| 201721_s_at | NM_006762 | Lysosomal-associated multispanning membrane protein-5 | LAPTM5 |
| 1555745_a_at | NM_000239 | lysozyme | LYZ |
| 213975_s_at | NM_000239 | lysozyme (renal amyloidosis) | LYZ |
| 208729_x_at | NM_005514 | major histocompatibility complex, class I, B | HLA-B |
| 211799_x_at | NM_002117 | major histocompatibility complex, class I, C | HLA-C |
| 217478_s_at | NM_006120 | major histocompatibility complex, class II, DM alpha | HLA-DMA |
| 203932_at | NM_002118 | major histocompatibility complex, class II, DM beta | HLA-DMB |
| 211991_s_at | NM_033554 | major histocompatibility complex, class II, DP alpha 1 | HLA-DPA1 |

TABLE 3-continued acute meta-signature.

| Affymetrix Ids | Accession Number | Gene name | Gene symbol |
|---|---|---|---|
| 201137_s_at | NM_002121 | major histocompatibility complex, class II, DP beta 1 | HLA-DPB1 |
| 211656_x_at | NM_002123 | major histocompatibility complex, class II, DQ beta 1 | HLA-DQB1 |
| 212998_x_at | NM_002123 | major histocompatibility complex, class II, DQ beta 1 | HLA-DQB1 |
| 209823_x_at | NM_002123 | major histocompatibility complex, class II, DQ beta 1 | HLA-DQB1 |
| 211654_x_at | NM_002123 | major histocompatibility complex, class II, DQ beta 1 | HLA-DQB1 |
| 208894_at | NM_019111 | major histocompatibility complex, class II, DR alpha | HLA-DRA |
| 210982_s_at | NM_019111 | major histocompatibility complex, class II, DR alpha | HLA-DRA |
| 215193_x_at | NM_022555 NM_021983 | major histocompatibility complex, class II, DR beta | HLA-DRB |
| 209312_x_at | NM_002124 NM_002125 | major histocompatibility complex, class II, DR beta | HLA-DRB |
| 204259_at | NM_002423 | matrix metalloproteinase 7 | MMP7 |
| 203471_s_at | NM_002664 | pleckstrin | PLEK |
| 203470_s_at | NM_002664 | pleckstrin | PLEK |
| 202659_at | NM_002801 | proteasome (prosome, macropain) subunit, beta 10 | PSMB10 |
| 209040_s_at | NM_004159 NM_148919 | proteasome (prosome, macropain) subunit, beta 8 | PSMB8 |
| 204279_at | NM_002800 NM_148954 | proteasome (prosome, macropain) subunit, beta 9 | PSMB9 |
| 207957_s_at | X06318 | protein kinase C, beta 1 | PRKCB1 |
| 209685_s_at | NM_002738 | protein kinase C, beta 1, transcript variant 2, mRNA. | PRKCB1 |
| 201858_s_at | NM_002727 | proteoglycan 1, secretory granule | PRG1 |
| 213603_s_at | NM_002872 | ras-related C3 botulinum toxin substrate 2 | Rac2 |
| 201288_at | NM_001175 | Rho GDP dissociation inhibitor beta | GDI |
| 204197_s_at | NM_004350 | runt-related transcription factor 3 | RUNX3 |
| 204198_s_at | NM_004350 | runt-related transcription factor 3 | RUNX3 |
| 209969_s_at | NM_139266 | signal transducer and activator of transcription 1, 91 kDa | STAT1 |
| 203761_at | NM_006748 | Src-like-adaptor | SLA |
| 203760_s_at | NM_006748 | Src-like-adaptor | SLA |
| 201645_at | NM_002160 | tenascin C | TNC |
| 237169_at | AL162425 | tenascin C | TNC |
| 201666_at | NM_003254 | TIMP metallopeptidase inhibitor 1 | TIMP1 |
| 205804_s_at | NM_025228 | TRAF3-interacting Jun N-terminal kinase | T3JAM |
| 213888_s_at | XM_514166 | TRAF3-interacting Jun N-terminal kinase (similar to) | T3JAM |
| 202307_s_at | NM_000593 | transporter 1, ATP-binding cassette, sub-family B | TAP1 |
| 206150_at | NM_001242 | tumor necrosis factor receptor superfamily, member 7 | CD27 |
| 205890_s_at | NM_006398 | ubiquitin D | UBD |

3.2 Classification and Prediction 3.2.1 Hierarchical Clustering Classification

To evaluate the power of this set of genes to classify acute samples compared to either borderline, normal or control samples, we performed a hierarchical clustering analysis of the different arrays in each subject analysis. The clustering was based on normalized value and standard correlation. Results are described for each dataset. Each row represents an subject probeset; each column, as an subject sample. Each tile in the heat map represents the expression level of a single gene in a single microarray. Red and green indicate that transcript levels are above and below the median for that gene across all the samples. Color saturation is proportional to the magnitude of the difference from the median. Because dataset D is based on ratio value rather than raw expression value the heat map appears different compared to the 4 other dataset analyses.

3.2.1.1 Dataset E-NHP

Figure 3:
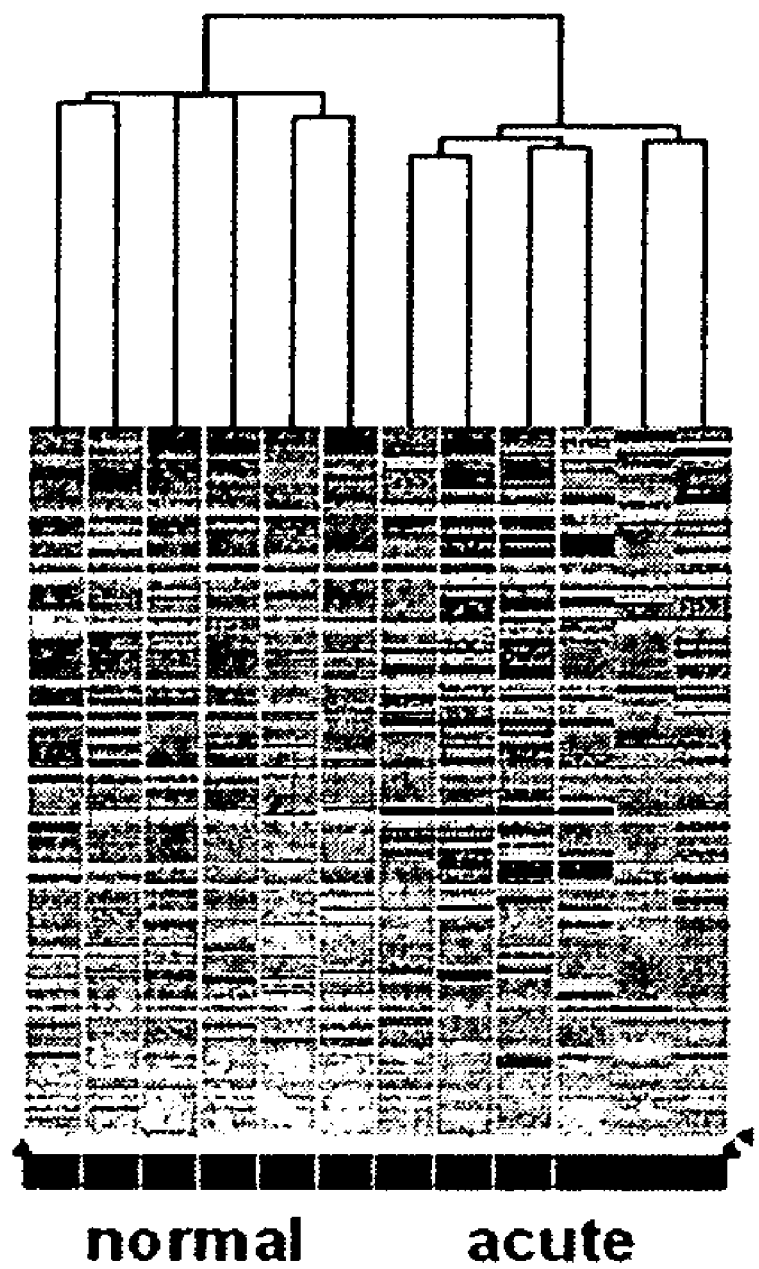
FIG. 3 is a hierarchical with clustering of dataset E-NHP.

Using the 81 probesets identified in the meta-analysis, hierarchical clustering analysis can separate perfectly with a high significance the acute rejected kidneys versus normal samples (FIG. 3). All the genes here are systematically up regulated during acute rejection. FIG. 3 shows the hierarchical clustering with standard correlation of the datasetE-NHP.

3.2.1.2 Dataset B

Figure 4:
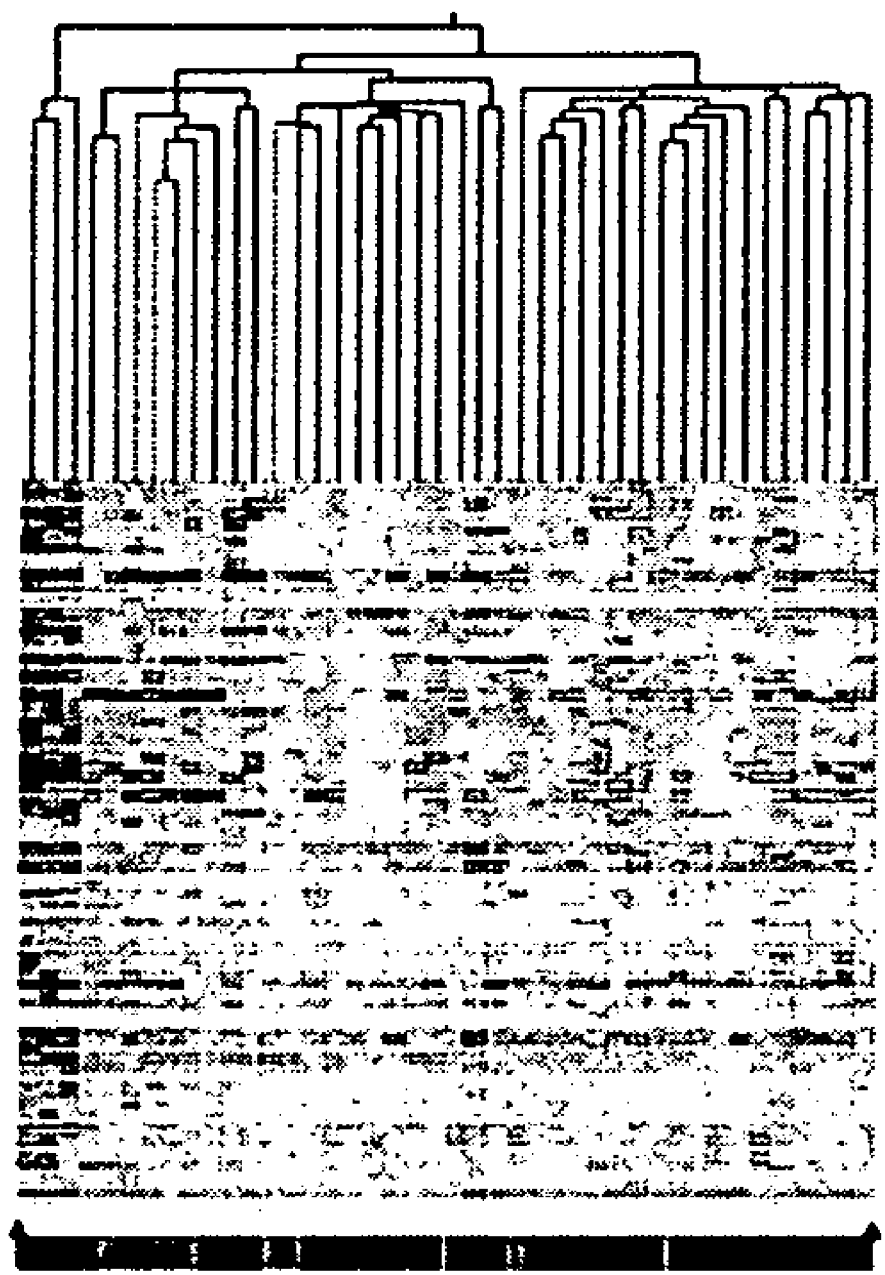
FIG. 4 is a hierarchical with clustering of dataset B.

Hierarchical clustering with the 81 probesets can correctly classify most of the acute and borderline versus normal samples (FIG. 4). One acute sample is classified with the borderline samples and 1 borderline sample is definitively classified with the normal samples. Interestingly, this clustering reveals 2 distinct groups of normal patients. One group shows no sign of up-regulation of the-meta signature genes. A second group clearly shows a mild up-regulation of these markers in a similar manner as borderline samples. FIG. 4 shows the hierarchical clustering with standard correlation of the dataset B.

3.2.1.3 Dataset C

Here, the meta-signature can correctly classify acute samples versus control, except one acute sample who behaves as a control sample (FIG. 5A). In this particular dataset borderline and control samples are highly similar for the low or absent expression of those genes and can be easily separated from acute samples (FIG. 5B). However one borderline samples is clearly classified as an acute sample. There was an opportunity to have a follow up on the evolution of the disease for these 2 misclassified patients.

Patient associated with chip 4058 was diagnosed as borderline in April the 29th but classified as acute by the genelist. A second diagnosis on July the 7th (2 month later) reveals that this patient underwent an acute episode. In this particular case, the gene expression change in the biopsy precedes the histological classification.

Figure 5:
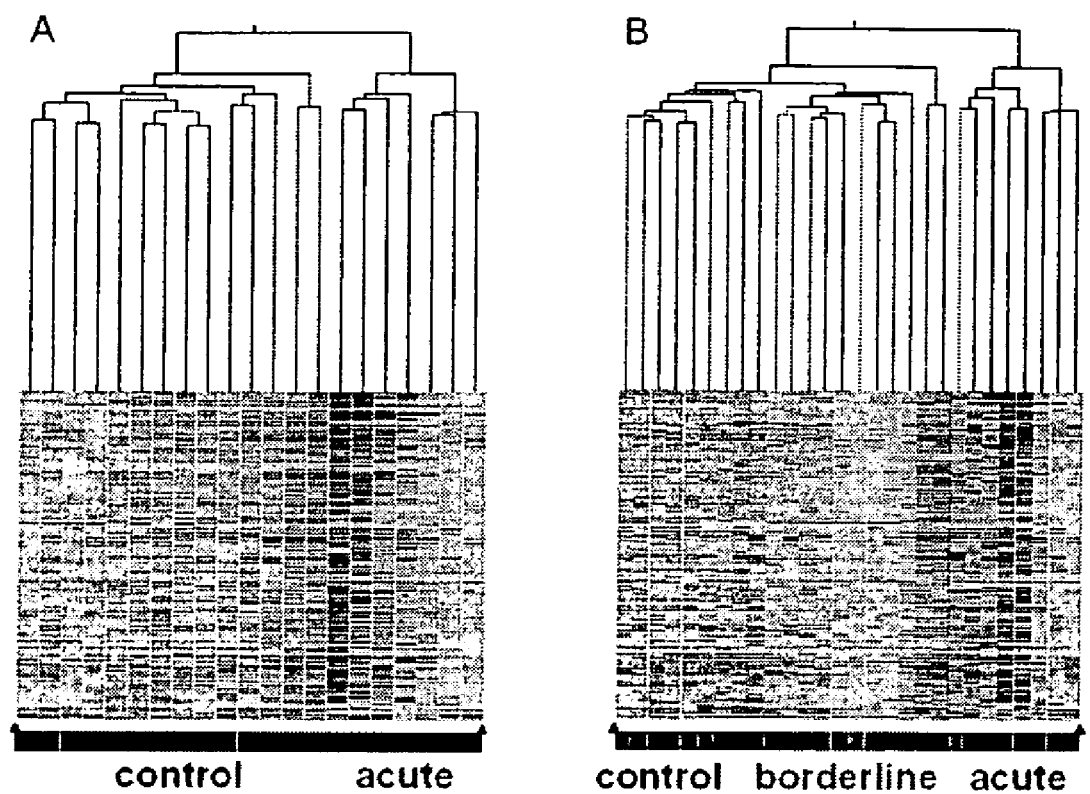
FIG. 5 is a hierarchical with clustering of dataset C.

Patient associated with chip 4044 was diagnoses as acute in April the 29th but is classified as borderline/normal by the genelist. Interestingly this patient has been diagnosed as borderline 2 month before (in February the 19th). In a same extend, another patient associated with chip 4076 was diagnosed as borderline in Nov. the 12th 2003 but classified as normal by the genelist. A second diagnosis on November the 21 th (9 days later) reveals that this patient was indeed classified as normal. In these two cases, the gene expression profile might provide a more accurate diagnostic than the first histological interpretation. FIG. 5 shows the hierarchical clustering with standard correlation of the datasetC. (A) control versus acute samples classification; (B) control versus borderline and acute samples classification.

3.2.1.4 Dataset A

Figure 6:
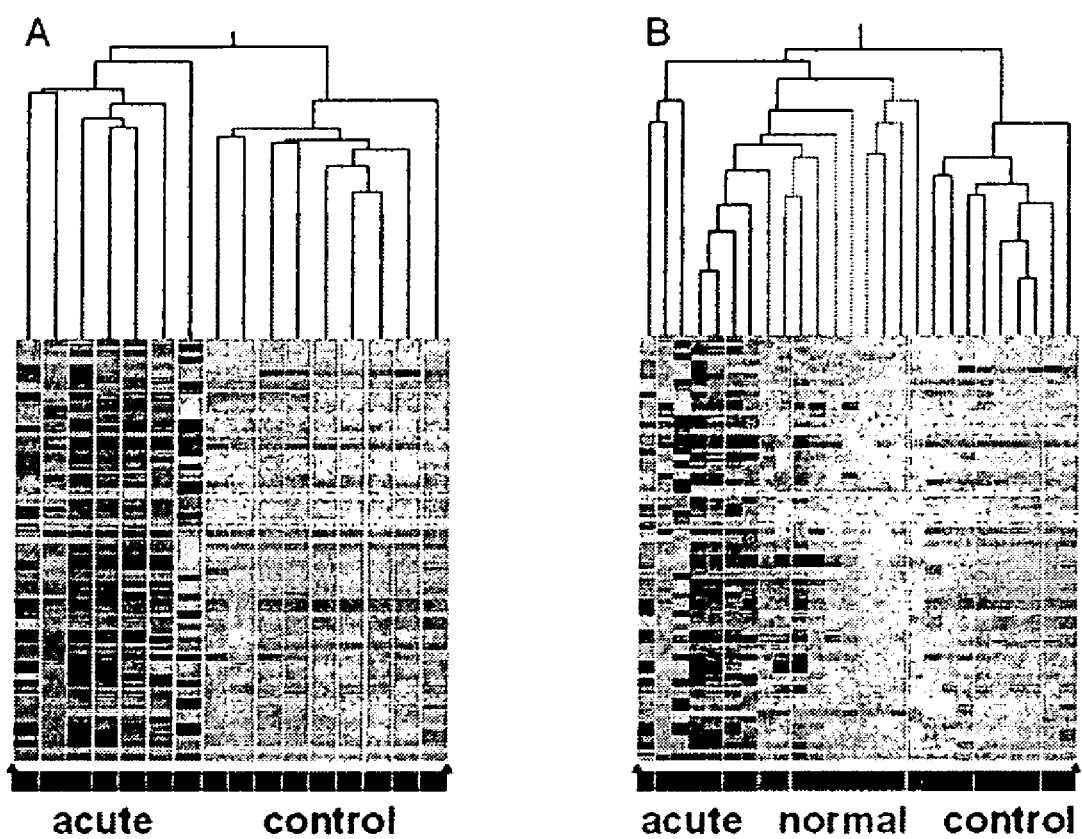
FIG. 6 is a hierarchical with clustering of dataset A.

The meta-signature can perfectly separate control kidneys versus acute rejected kidneys (FIG. 6A). Here also we can observe a discrepancy in the normal group (FIG. 6B). On group shows no expression of those genes and are similar to control samples, and one other group presents a gradient of expression from control to acute stage. FIG. 6 shows the hierarchical clustering with standard correlation of datasetA. (A) control versus acute samples classification; (B) control versus normal and acute samples classification.

3.2.1.5 Dataset D

Figure 7:
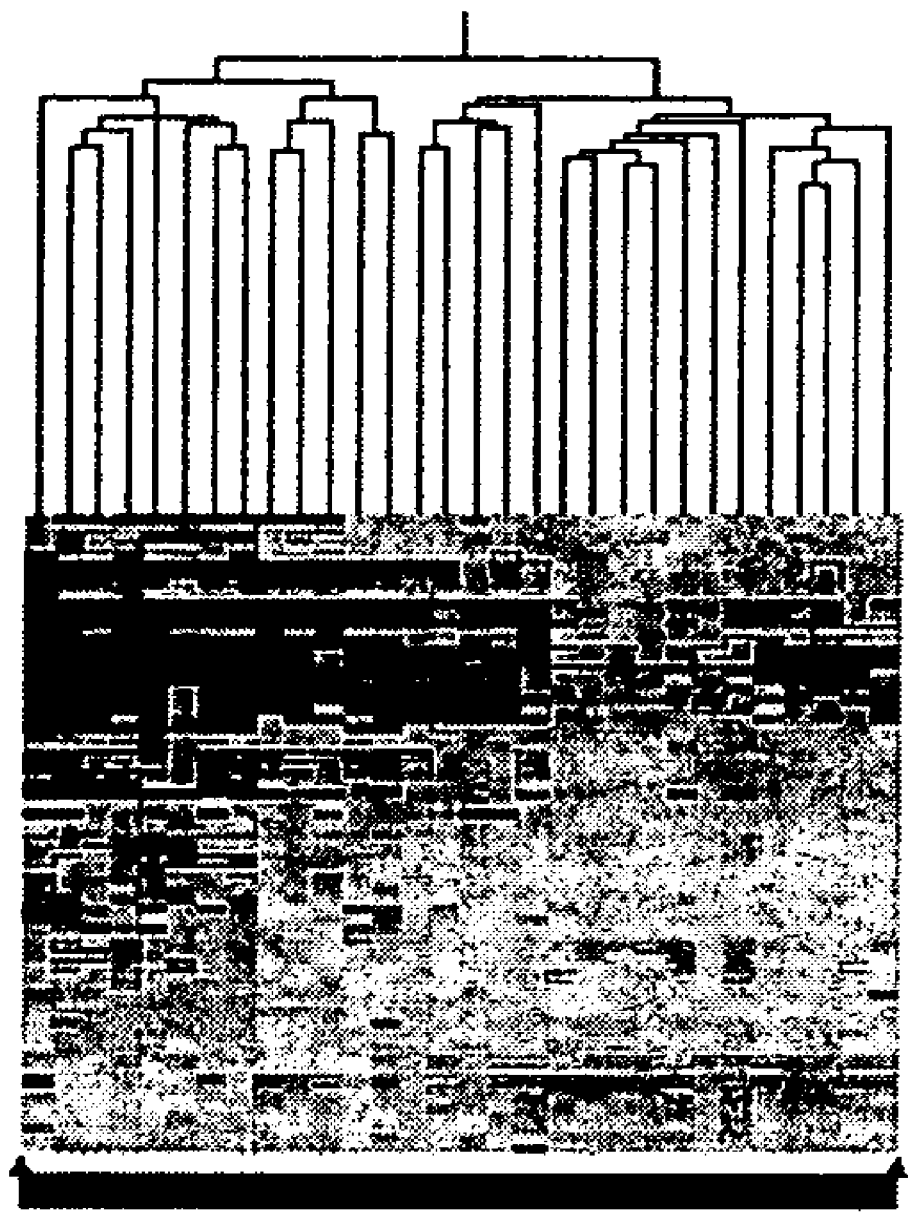
FIG. 7 is a hierarchical with clustering of dataset D.

The meta-signature can classify most of the acute versus normal samples correctly (FIG. 7). Two clear groups of acute and normal samples are well separated whereas one intermediate group of 2 acute and 3 control samples might behave as borderline. Here again the separation is based on a gradient of up regulated genes. FIG. 7 shows the hierarchical clustering with standard correlation of dataset D.

In summary, hierarchical clustering shows that the combination of 81 probesets (see table 3) is capable of classifying acute versus control, normal and borderline samples most correctly in all the 5 re-analyzed datasets. This result suggests a strong diagnostic properties for this meta-signature. The classification is always associated with a gradient of up regulated genes from no expression in control and normal samples, to a mild expression in borderline samples and then a strong up regulation in fully acute rejected samples. It is also important to mention that normal transplanted patients are often classified in two different groups regarding this gene expression profile (either similar to control or borderline samples). This observation should have an impact in the validation of this meta-signature as diagnostic tool.

3.2.2 Prediction with Support Vector Machine (SVM) Algorithm

To further validate if this expression pattern of 81 probesets can be used as a tool to predict the outcome of acute rejection, we used the Class Prediction function in GeneSpring. The Class Predictor is designed to predict the value, or "class" of an subject parameter in an uncharacterized samples or set of samples. Seven AR+CR samples were then tested from dataset C. These samples present histological signs of acute rejection and, on top of that, additional signs of chronic rejection. Because those samples were never included in the analysis, they were considered as being totally independent and suitable for a real predictive test. Using the SVM prediction function (Golub, T. R. et. al. "Molecular Classification of Cancer: Class Discovery and Class Prediction by Gene Expression Monitoring" Science, v286, pp 531-537 (1999)), and the "control, borderline, acute" comparison (from dataset A) as training set, 5 of the 7 AR+CR samples were predicted as acute. One sample is predicted as borderline and one as control.

4 CONCLUSION

These results show that after meta-analysis of 5 different datasets, a common transcriptomic profile of kidney acute rejection was identified This profile includes 81 probesets (corresponding to 57 genes) that are up-regulated in all analyzed acute samples. These meta-signature genes are highly related to biological mechanisms known to be crucial for the development of allograft rejection and are able to correctly classify acute versus normal samples in the 5 independent studies. Therefore, the result of this meta-analysis provides a robust combination of gene expression suitable for diagnosis of acute allograft rejection.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for assessing the onset of rejection of a transplanted organ in a subject, comprising:
  a) determining the magnitude of gene expression of the following genes:
    (1) caspase 1, apoptosis-related cysteine peptidase (CASP1) ($NM\_001223$; NM_033292);
    (2) caspase 1, apoptosis-related cysteine peptidase (CASP1) (NM_033293);
    (3) caspase 1, apoptosis-related cysteine peptidase (CASP1) (NM_033294; NM_033295);
    (4) similar to caspase 1, apoptosis-related cysteine protease (CASP1) (BU675703);
    (5) CD44 antigen, transcript variant 1 and 2, mRNA (CD44) (NM_001001389; NM_000610);
    (6) CD44 antigen transcript variant 3 and 4, mRNA (CD44) (NM_001001390; NM_001001391);
    (7) CD48 antigen (CD48) (NM_001778);
    (8) CD52 antigen (CD52) (NM_001803);
    (9) CD53 antigen (CD53) (NM_000560);
    (10) CD53 antigen (CD53) (AL391064);
    (11) CD8 antigen, alpha (CD8A) (NM_171827; NM_001768);
    (12) cDNA clone IMAGE: 387863 (BM684568);
    (13) chemokine (C-C motif) ligand 5 (CCL5) (NM_002985);
    (14) chemokine (C-X-C motif) ligand 10 (CXCL10) (NM_001565);
    (15) chemokine (C-X-C motif) ligand 9 (CXCL9) (NM_002416);
    (16) chondroitin sulfate proteoglycan 2 (CSPG2) (NM_004385);

(17) cytochrome b-245, beta polypeptide (CYBB) (NM_000397);
(18) glia maturation factor, gamma (GMFG) (NM_004877);
(19) granzyme A (GZMA) (NM_006144);
(20) guanylate binding protein 1, interferon-inducible, 67 kDa (GBP1) (NM_002053);
(21) similar to guanylate binding protein 2, interferon-inducible (GBP2) (AL832451);
(22) hematopoietic cell-specific Lyn substrate 1 (HCLS1) (NM_005335);
(23) hematopoietic cell kinase (HCK) (NM_002110);
(24) similar to IgM heavy chain (IGHM) (BC089412);
(25) similar to immunoglobulin alpha 1 heavy chain (IGHA1) (S55735);
(26) similar to immunoglobulin heavy constant mu (IGHM) (XM_522973);
(27) integrin, beta 2 (ITGB2)(NM_000211);
(28) interferon stimulated gene 20 kDA (ISG20) (NM_02201);
(29) interleukin 10 receptor, alpha (IL10RA) (NM_001558);
(30) lymphocyte cytosolic protein 1 (L-plastin) (NM_002298);
(31) lymphocyte cytosolic protein 2 (SLP76) (NM_005565);
(32) lymphocyte-specific protein tyrosine kinase (LCK) (NM_005356);
(33) lysosomal-associated multispanning membrane protein-5 (LAPTM5) (NM_006762);
(34) lysozyme (LYZ) (NM_000239);
(35) major histocompatibility complex, class I, B (HLA-B) (NM_005514);
(36) major histocompatibility complex, class I, C (HLA-C) (NM_002117);
(37) major histocompatibility complex, class II, DM alpha (HLA-DMA) (NM_006120);
(38) major histocompatibility complex, class II, DM beta (HLA-DMB) (NM_002118);
(39) major histocompatibility complex, class II, DP alpha 1 (HLA-DPA1) (NM_033554);
(40) major histocompatibility complex, class II, DP beta 1 (HLA-DPB1) (NM_002121);
(41) major histocompatibility complex, class II, DQ beta 1 (HLA-DQB1) (NM_002123);
(42) major histocompatibility complex, class II, DR alpha (HLA-DRA) (NM_019111);
(43) major histocompatibility complex, class II, DR beta (HLA-DRB) (NM_022555; NM_021983);
(44) major histocompatibility complex, class II, DR beta (HLA-DRB) (NM_002124; NM_002125);
(45) matrix metalloproteinase 7 (MMP7) (NM_002423);
(46) pleckstrin (PLEK) (NM_002664);
(47) proteasome (prosome, macropain) subunit, beta 10 (PSMB10) (NM_002801);
(48) proteasome (prosome, macropain) subunit, beta 8 (PSM8) (NM_004159; NM_148919);
(49) proteasome (prosome, macropain) subunit, beta 9 (PSMB9) (NM_002800; NM_148954);
(50) protein kinase C beta 1 (PRKCB1) (X06318);
(51) protein kinase C beta 1, transcript variant 2, mRNA (PRKCB1) (NM_002738);
(52) proteoglycan 1, secretory granule (PRG1) (NM_002727);
(53) ras-related C3 botulinum toxin substrate 2 (Rac2) (NM_002872);
(54) Rho GDP dissociation inhibitor beta (GDI) (NM_001175);
(55) runt-related transcription factor 3 (RUNX3) (NM_004350);
(56) signal transducer and activator of transcription 1, 91 kDa (STAT1) (NM_139266);
(57) Src-like-adaptor (SLA) (NM_006748);
(58) tenascin C (TNC) (NM_002160);
(59) tenascin C (TNC) (AL162425);
(60) TIMP metallopeptidase inhibitor 1 (TIMP1) (NM_003254);
(61) TRAF3-interacting Jun N-terminal kinase (T3JAM) (NM_025228);
(62) similar to TRAF3-interacting Jun N-terminal kinase (T3JAM) (XM_514166);
(63) transporter 1, ATP-binding cassette, sub-family B (TAP1) (NM_000593);
(64) tumor necrosis factor receptor superfamily, member 7 (CD27) (NM_001242); and
(65) ubiquitin D (UBD) (NM_006398)
in a post-transplantation sample from the subject;
  b) comparing the magnitude of gene expression of the genes set forth in a) in the post-transplantation sample with the magnitude of gene expression of the same genes in a control sample; and
  c) determining whether the magnitude of gene expression of the genes set forth in a) is up-regulated relative to the control sample, wherein up-regulation of the genes set forth in a) indicates that the subject is likely to experience transplant rejection, thereby assessing the onset of rejection of the transplanted organ in the subject.

2. The method of claim 1, wherein the sample comprises cells obtained from the subject.

3. The method of claim 1, wherein the sample is a graft biopsy.

4. The method of claim 1, wherein the sample is selected from the group consisting of blood, serum, and urine.

5. The method of claim 1, wherein the magnitude of expression in the sample differs from the control magnitude of expression by a factor of at least about 2.

6. The method of claim 1, wherein the magnitude of expression in the sample differs from the control magnitude of expression by a factor of at least abut 3.

7. The method of claim 1, wherein the post-transplantation sample is a graft biopsy.

8. The method of claim 1, wherein the rejection is an acute rejection.

9. The method of claim 8, wherein the acute rejection is an early acute rejection.

10. The method of claim 1, wherein the subject is a human patient.

11. The method of claim 1, wherein the transplanted organ is a kidney.

12. The method according to claim 1, wherein the magnitude of gene expression is assessed by detecting the presence of a protein encoded by the gene.

13. The method according to claim 12, wherein the presence of the protein is detected using a reagent which specifically binds to the protein.

14. The method according to claim 1, wherein the magnitude of gene expression is detected by techniques selected from the group consisting of Northern blot analysis, reverse transcription PCR and real time quantitative PCR.

* * * * *